US007723255B2

(12) United States Patent
Hoveyda et al.

(10) Patent No.: US 7,723,255 B2
(45) Date of Patent: *May 25, 2010

(54) RECYCLABLE METATHESIS CATALYSTS

(75) Inventors: Amir H. Hoveyda, Belmont, MA (US); Jason Kingsbury, Brookline, MA (US); Steven Garber, Brighton, MA (US); Brian Lawrence Gray, Chestnut Hill, MA (US); John T. Fourkas, Chestnut Hill, MA (US)

(73) Assignee: The Trustees of Boston College, Chestnut Hill, MA (US)

( * ) Notice: Subject to any disclaimer, the term of this patent is extended or adjusted under 35 U.S.C. 154(b) by 1275 days.

This patent is subject to a terminal disclaimer.

(21) Appl. No.: 11/178,884

(22) Filed: Jul. 11, 2005

(65) Prior Publication Data

US 2005/0272598 A1    Dec. 8, 2005

Related U.S. Application Data

(62) Division of application No. 09/925,555, filed on Aug. 9, 2001, now Pat. No. 6,921,735.

(60) Provisional application No. 60/264,361, filed on Jan. 26, 2001, provisional application No. 60/224,305, filed on Aug. 10, 2000.

(51) Int. Cl.
    *B01J 31/18*    (2006.01)
(52) U.S. Cl. .......................... 502/155; 502/152; 502/87
(58) Field of Classification Search ................ 502/152, 502/155, 87
See application file for complete search history.

(56) References Cited

U.S. PATENT DOCUMENTS 6,310,121 B1 *  10/2001  Woodson et al. .............. 524/32

6,921,735 B2 *  7/2005  Hoveyda et al. ............. 502/152

OTHER PUBLICATIONS

Garber, et al., Efficient and Recyclable Monomeric and Dendritic Ru-Based Metathesis Catalysts, *Journal of the American Chemical Society*, vol. 122, No. 34: 8168-8179 (2000).
Gessler, et al., Synthesis and Metathesis Reactions of a Phosphine-free Dihydroimidazole Carbene Ruthenium Complex, *Tetrahedron Letters*, No. 51: 9973-9976 (2000).
Harrity, et al., Chromenes through Metal-Catalyzed Reactions of Styrenyl Ethers, Mechanism and Utility in Synthesis, *Journal of the American Chemical Soceity*, vol. 120, No. 10: 2343-2351 (1997).
Harrity, et al., Ru-Catalyzed Rearrangement of Styrenyl Ethers. Enantioselective Synthesis of Chromenes through Zr- and Ru-Catalyzed Processes, *Journal of the American Chemical Society*, vol. 119; 1488-1489 (1996).
Kingsbury, et al., A Recyclable Ru-Based Metathesis Catalyst, *Journal of the American Chemical Society*, vol. 121, No. 4: 791-799 (1998).
Randl, et al., Highly Selective Cross Metathesis with Acrylonitrile Using a Phosphine Free Ru-Complex, *Synlett*, No. 3: 430-432 (2000).
International Search Report PCT/US01/24955.

* cited by examiner

*Primary Examiner*—Ling-Siu Choi
(74) *Attorney, Agent, or Firm*—Edwards Angell Palmer & Dodge LLP; Jeffrey D. Hsi; Mark D. Russett

(57) ABSTRACT

Highly active, recoverable and recyclable transition metal-based metathesis catalysts and their organometallic complexes including dendrimeric complexes are disclosed, including a Ru complex bearing a 1,3-dimesityl-4,5-dihydroimidazol-2-ylidene and styrenyl ether ligand. The heterocyclic ligand significantly enhances the catalytic activity, and the styrenyl ether allows for the easy recovery of the Ru complex. Derivatized catalysts capable of being immobilized on substrate surfaces are also disclosed. The present catalysts can be used to catalyze ring-closing metathesis (RCM), ring-opening (ROM) and cross metatheses (CM) reactions, and promote the efficient formation of various trisubstituted olefins at ambient temperature in high yield.

30 Claims, 4 Drawing Sheets

RECYCLABLE METATHESIS CATALYSTS

RELATED APPLICATIONS

This application is a divisional of U.S. patent application Ser. No. 09/925,555, filed on Aug. 9, 2001 which claims the benefit of U.S. Provisional Application No. 60/264,361 filed on Jan. 26, 2001 and U.S. Provisional Application No. 60/224,305 filed on Aug. 10, 2000.

GOVERNMENT SUPPORT

This invention was supported by a grant from the National Science Foundation. The government has certain rights in this invention.

BACKGROUND OF THE INVENTION

Metal-catalyzed olefin metathesis reactions serve as a springboard for the development of a range of regioselective and stereoselective processes. These processes are important steps in the chemical synthesis of complex organic compounds and polymers. In particular, these reactions often are crucial steps in medicinal chemistry for small molecule synthesis. Organometallic catalysts, particularly transition metal complexes based on osmium, ruthenium or tungsten, are used in many such organic transformation reactions.

The synthesis and catalytic activity of ruthenium-based complexes which can efficiently catalyze ring-opening metathesis (ROM) and ring-closing metathesis (RCM) of dienes that contain terminal olefins has been reported for example, by Kingsbury, J. S.; Harrity, J. P. A.; Bonitatebus, P. J.; Hoveyda, A. H. *J. Am. Chem. Soc.* 1999, 121, 791-799; Harrity, J. P. A.; Visser, M. S.; Gleason, J. D.; Hoveyda, A. H. *J. Am. Chem. Soc.* 1997, 119, 1488-1489; and Harrity, J. P. A.; La, D. S.; Cefalo, D. R.; Visser, M. S.; Hoveyda, A. H. *J. Am. Chem. Soc.* 1998, 120, 2343-2351. Because of the risk of metal contamination of the resulting product, and due to the cost of organometallic catalysts, recovery and reuse of such catalysts is important. Kingsbury, et al. showed that an organometallic ruthenium-based catalyst could be recovered from the reaction mixture by silica gel chromatography in high yield and reused in subsequent C—C bond forming reactions. Kingsbury et al., supra. However, there are several shortcomings in the prior art recyclable metathesis catalyst, including that it is useful mostly for substrates that contain terminal alkenes. In certain cases, due to co-elution, isolation of the catalyst from the substrate is problematic.

SUMMARY OF THE INVENTION

The present invention comprises highly active and recyclable transition metal-based metathesis catalysts, methods of making such catalysts and their use in metathesis reactions. The catalysts of the present invention are organometallic complexes of a transition metal comprising an organic ligand that permits recovery of the catalyst metal from the reaction mixture. The organometallic complexes of the invention can be in monomeric, polymeric and dendritic forms that are capable of promoting various forms of metathesis reactions in a highly efficient manner, and can be efficiently recovered from the reaction mixtures and reused; they are therefore, recyclable. Unlike prior recoverable transition metal-based complexes, the catalysts of the present invention effect the efficient formation of trisubstituted alkenes and tetrasubstituted olefins through catalytic metathesis processes. The polymeric and dendritic catalysts of the invention offer the added advantage that they are more readily insoluble. The present catalysts are extremely active (can be used to prepare tri- and tetra-substituted olefins), can be readily recovered and reused and leave little or no trace of toxic metal contamination within the product.

In one aspect, the invention comprises a composition comprising a monomeric catalyst having the following Formula I:

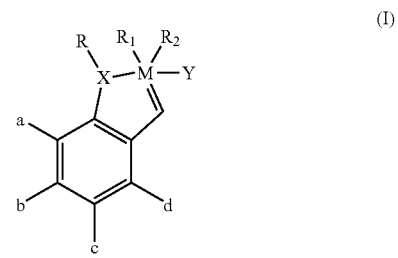

(I)

wherein:

M is a transition metal;

X comprises oxygen (O), sulfur (S), nitrogen (N) or phosphorus (P);

R comprises an alkyl, alkenyl, alkynyl, aryl, alkoxy, alkenyloxy, alkynyloxy, aryloxy, alkoxy carbonyl, alkylamino, alkylthio, alkylsulfonyl, alkylsulfinyl; each optionally substituted with an alkyl, halogen, alkoxy, aryl or heteroaryl moiety;

$R_1$ and $R_2$ each comprise, or together comprise, an electron withdrawing anionic ligand;

a, b, c, and d each comprises H, a halogen atom or an alkyl, alkenyl, alkynyl, aryl, alkoxy, alkenyloxy, alkynyloxy, aryloxy, alkoxycarbonyl, alkylamino, alkylthio, alkylsulfunyl; alkylsulfinyl; each optionally substituted with an alkyl, halogen, aryl or heteroaryl moiety; and Y comprises an electron-donating heterocyclic carbene ligand.

In a preferred embodiment, M is ruthenium, X is O, R is a lower alkyl group (e.g., $C_1$-$C_{12}$), $R_1$ and $R_2$ are halogen atoms (which may be identical or different but preferably are identical), a, b, c and d each comprises hydrogen or a lower alkyl group (e.g., $C_1$-$C_{12}$), and Y comprises a 4,5-dihydroimidazol-2-ylidene carbene ligand ring structure or a phosphine moiety. In a more preferred embodiment, M is ruthenium, X is O, R is isopropyl, $R_1$ and $R_2$ are chlorine atoms (Cl), a, b, c and d each comprises hydrogen, and Y comprises a heterocyclic ring structure having the following Formula II:

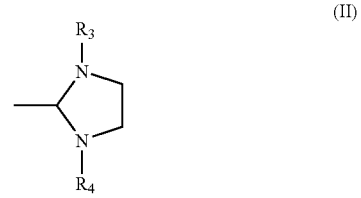

(II)

wherein $R_3$ and $R_4$ comprise the same or different aromatic ring moieties. In a currently preferred embodiment, $R_3$ and $R_4$ both comprise 2,4,6-trimethylphenyl (mesityl) moieties.

In another aspect, the invention comprises dendritic catalyst structure having the following Formula III:

wherein $R_5$, $R_6$, $R_7$ and $R_8$ each comprises the following Formula IV:

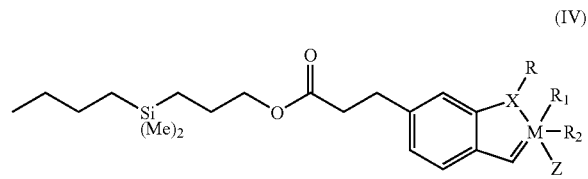

wherein:
M comprises a transition metal;
X comprises O, S, N or P;
R comprises an alkyl, alkenyl, alkynyl, aryl, alkoxy, alkenyloxy, alkynyloxy, aryloxy, alkoxy carbonyl, alkylamino, alkylthio, alkylsulfunyl, alkylsulfinyl; each optionally submitted with an alkyl, halogen, aryl or heteroaryl moiety;
$R_1$ and $R_2$ each comprises, or together comprise, an electron withdrawing group; and Z comprises Y or a phosphine group.

In a preferred embodiment, M is Ru, X is O, R is a lower alkyl group (e.g., $C_1$-$C_{12}$), $R_1$ and $R_2$ are halogen atoms (which may be identical or different but preferably are identical), and Z comprises a phosphine moiety having the formula P(Cy)$_3$, wherein Cy comprises an aliphatic ring structure, preferably cyclohexyl or cyclopentyl. In a currently preferred embodiment, M is Ru, X is O, R is isopropyl, $R_1$ and $R_2$ each is a chlorine atom (Cl), and Z is P(cyclohexyl)$_3$.

In another preferred embodiment, M is Ru, X is O, R is a lower alkyl group (e.g., $C_1$-$C_{12}$), $R_1$ and $R_2$ are halogen atoms and Z comprises a ring structure having Formula II wherein $R_3$ and $R_4$ comprise the same or different aromatic ring moieties. In a currently preferred embodiment, M is Ru, X is O, R is isopropyl, $R_1$ and $R_2$ are chlorine atoms (Cl) and Z comprises a ring structure having Formula II wherein $R_3$ and $R_4$ both comprise a 2,4,6-trimethyl phenyl (mesityl) moiety.

The present invention provides stable, readily recoverable transition metal-based metathesis catalysts with high catalytic activity. The catalysts may be used free in the reaction mixture or may be immobilized on a solid phase. In another aspect of the invention, the monomeric catalysts of Formula I are immobilized on a solid phase. In a preferred embodiment, the catalysts of the invention are immobilized on solid phases such as, for example, metals, glass, polymers, ceramics, organic polymer beads, inorganic sol-gels or other inert substances, without impairing their ability to catalyze various forms of metathesis reactions in a highly efficient manner. In a currently preferred embodiment, the solid phase is an inorganic sol gel such as, for example, a glass monolithic gel. In addition, the invention comprises the design and synthesis of various chiral versions of the present monomeric and dendritic complexes and their application to asymmetric catalytic metathesis.

Immobilization of catalysts of the invention to an inorganic monolithic gel provides the following advantages over immobilization of such catalysts on conventional solid phases such as organic polymer beads: (1) overcomes limitations of organic polymer beads such as variable swelling and shrinking in different media, often resulting in reduction of catalytic activity (2) precludes the addition of significant volumes of solvents needed for recovery of beads bound to the catalyst, a necessity that seriously limits the utility of recoverable surface immobilized catalysts, thereby detracting from the practicality of such an approach and rendering it more costly and environmentally less friendly. (3) The high porosity characteristic of inorganic gels translates to a substantially large interfacial surface area (typically 300-1000 m$^2$/g), rendering such materials ideal for immobilization of catalysts of the invention. (4) Gelation occurs after a sol is cast into a mold; it is, therefore, possible to tailor the gel samples to a desired shape or even function.

In another preferred embodiment, the surface immobilized catalysts of the present invention is an integral part of the reaction apparatus itself, thus obviating the need for a filtration step to recover the catalyst after completion of metathesis processes. Processes of the present invention are, therefore, rendered operationally simple from the standpoint of both execution and work-up.

The recyclable catalysts of the present invention are substantially more active than prior art recyclable metathesis catalysts. The transition metal-based monomers and dendrimers of the present invention are easily characterizable and serve as homogeneous metathesis catalysts that are highly active and allow for significantly more facile catalyst recovery compared to prior art catalysts.

DETAILED DESCRIPTION OF THE INVENTION

The present invention comprises a novel class of recoverable and recyclable organometallic metathesis catalysts. The term "recoverable" as used herein means that the catalyst can be recovered or retrieved from the reaction mixture once the reaction is complete. The term "recyclable" means that the recovered catalyst can be reused in subsequent metathesis reactions after recovery from the previous reaction(s).

The catalysts of the present invention comprise novel monomeric catalysts having the structure of Formula I, and dendritic catalysts having the structure of Formula III. The present monomeric and dendritic catalysts are recoverable and recyclable, and can efficiently catalyze a variety of olefin metathesis reactions, including ring-opening metathesis (ROM), ring-closing metathesis (RCM), cross-metathesis (CM), ring-opening polymerization metathesis (ROMP), and acyclic diene metathesis (ADMET). The catalysts of the present invention can be used in most metathesis reactions under appropriate conditions. Those skilled in the art would be able to empirically determine the amount of catalyst and optimal conditions of the reaction. For example, the monomeric and dendritic catalysts of the present invention can be used in most reactions at levels of from about 1.0 mol % to about 5.0 mol %.

The present catalysts can be recovered from the reaction mixture by any technique suitable for recovering or separating organometallic complexes, including chromatography or filtration. For example, the monomeric or dendritic catalysts may be separated form the reaction mixture by silica gel chromatography. If the catalyst is attached to a solid phase, as described below, then the catalyst can be recovered by separating the solid phase from the reaction mixture by simple filtration.

Monomeric complexes. In one aspect, the present invention provides monomeric catalysts having the structure shown as Formula I. Monomeric catalysts having Formula I can be prepared according to the procedures shown in Equation 1 below, in Examples 1-10, or via other synthetic routes that would be readily ascertainable by those skilled in the art.

The structure shown as Formula 5 in Equation 1 below comprises a currently preferred embodiment of the present invention.

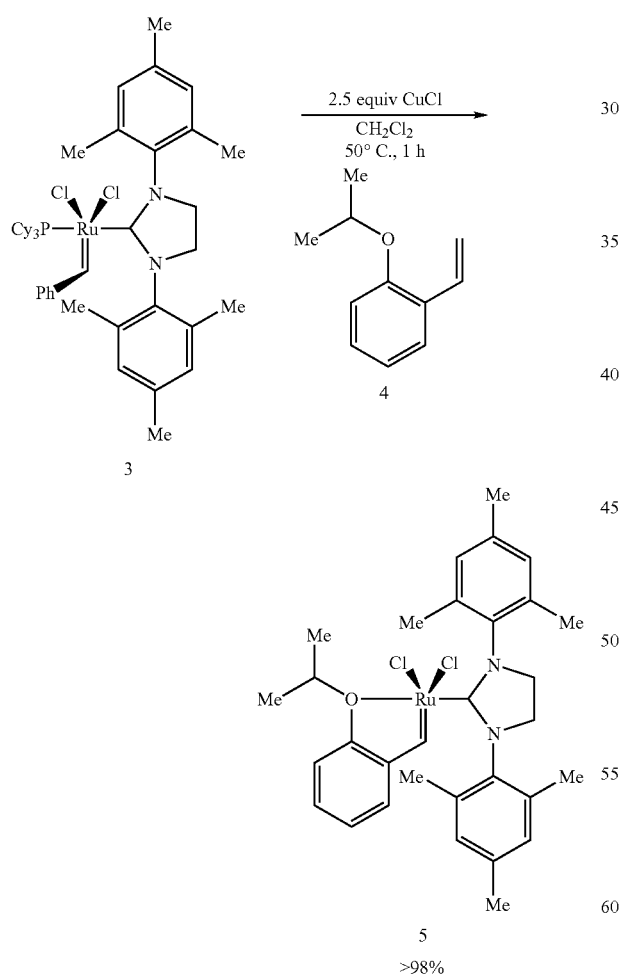

Equation 1 imidazolin-2-ylidene and unsaturated imidazol-2-ylidene carbene ligands accelerated the metathetic activity of Ru-based complexes. As depicted in Equation 1, treatment of compound 3 with 2.5 equivalents CuCl and 0.97 equivalents of compound 4 in $CH_2Cl_2$ at 40° C. delivers the Formula 5 catalyst within 1 hour; the Formula 5 catalyst was isolated as an air stable green solid in quantitative (>98%) yield after silica gel chromatography (mp=178-181° C. dec).

Figure 2:
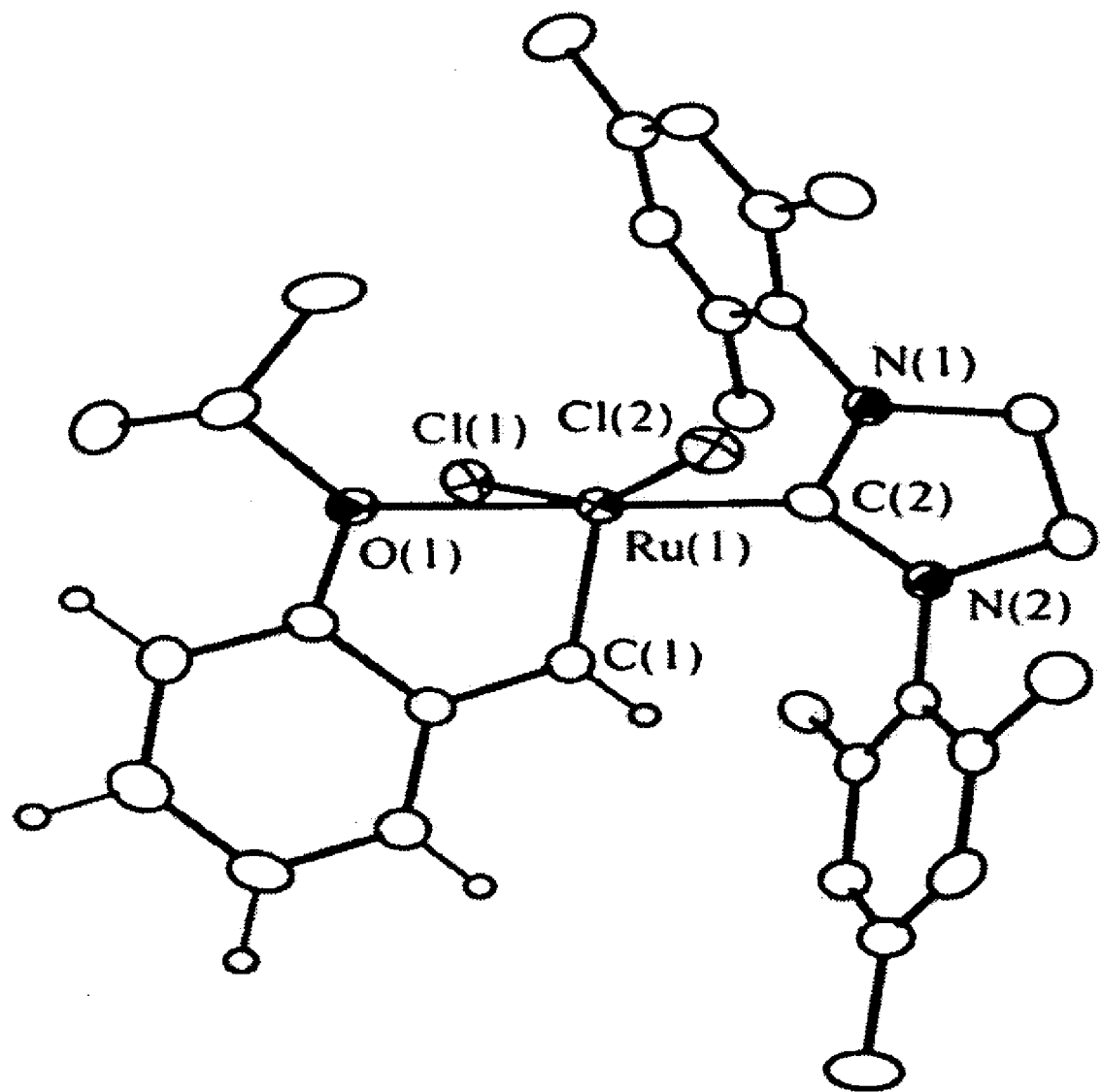
FIG. 2 shows an ORTEP diagram of Cl$_2$Ru(=CH-o-OiPrC$_6$H$_4$)(4,5-dihydroIMES) (Formula 5). Thermal ellipsoids are drawn at 30% probability level, and selected bond distances and angles are shown in Table 1.

Single-crystal X-ray structure analysis of a Formula 5 catalyst is shown in FIG. 2; (IMES=1,3-bis(2,4,6-trimethylphenyl)imidazol-2-ylidene). The crystal structure analysis confirms the structural assignment shown in Formula 5. Selected bond lengths and angles for Formula 5 are provided in Table 1. The overall geometry around the transition metal center and most of the bond angles and bond lengths in Formula 5 are analogous to their related values in the complex of Formula 6 (shown in Scheme 1).

Figure 1:
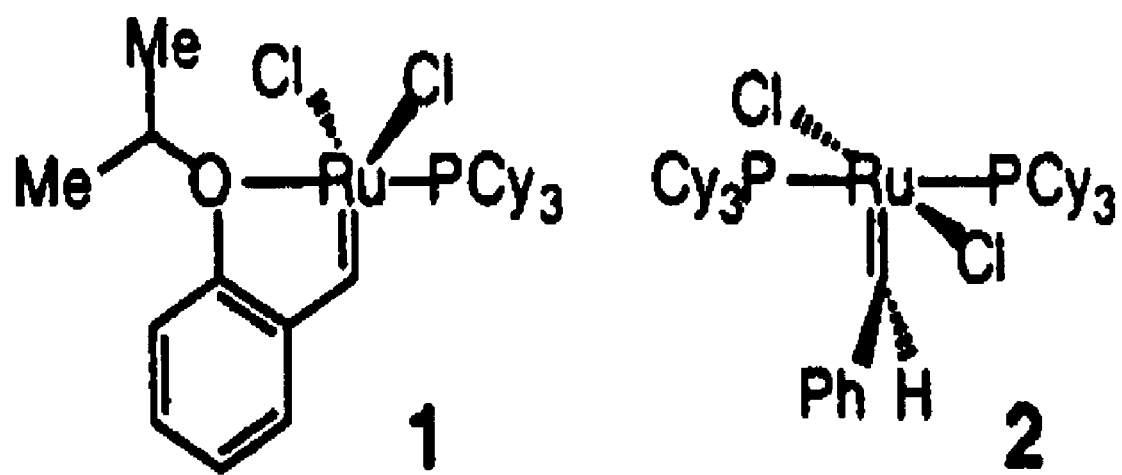
FIG. 1 shows two prior art ruthenium catalysts: (1) is a recoverable complex of ruthenium with an isopropoxystyrene and a phosphine moiety, and (2) is a benzylidene catalyst.

Comparison of the $^1H$ NMR spectra of prior art compound 1 (shown in FIG. 1) and the Formula 5 catalyst show some of the differential structural attributes of these complexes. As illustrated in Scheme 1, there are two distinct chemical shift changes in the 400 MHz $^1H$ NMR spectra of Formula 5 catalyst and compound 1. One variation is observed at the iso-Pr methine proton and another at the carbene $CH(H_\alpha)$. In both instances, the protons for the imidazolin-2-ylidene system in Formula 5 are more shielded. These differences may be attributed to higher electron density at the transition metal center of Formula 5, caused by the stronger electron donation by the heterocyclic ligand (compared to $PCy_3$ (Cy is an aliphatic cycloalkyl moiety, preferably cyclohexyl). The weaker electron donation by the oxygen ligand to the Ru center in Formula 5 may be manifested by the more upfield appearance of the isopropyl methine proton (5.28 vs 4.90 ppm).

TABLE 1

Selected Bond Lengths and Angles for
$Cl_2Ru(=CH-o-OiPrC_6H_4)(4,5-dihydroIMES)$ (Formula 5)

| Bond lengths (Å) | | | |
|---|---|---|---|
| Ru(1)-C(1) | 1.828(5) | Ru(1)-Cl(1) | 2.328(12) |
| Ru(1)-C(2) | 1.981(5) | Ru(1)-Cl(2) | 2.340(12) |
| Ru(1)-O(1) | 2.261(3) | C(2)-N(1) | 1.351(6) |
| | | C(2)-N(2) | 1.350(6) |
| Bond angles (deg) | | | |
| C(1)-Ru(1)-O(1) | 79.3(17) | O(1)-Ru(1)-Cl(1) | 86.9(9) |
| C(1)-Ru(1)-C(2) | 101.5(14) | O(1)-Ru(1)-Cl(2) | 85.3(9) |
| C(2)-Ru(1)-O(1) | 176.2(14) | C(2)-Ru(1)-Cl(1) | 96.6(12) |
| C(1)-Ru(1)-Cl(1) | 100.2(15) | C(2)-Ru(1)-C(2) | 90.9(12) |
| C(1)-Ru(1)-Cl(2) | 100.1(15) | Cl(1)-Ru(1)-Cl(2) | 156.5(5) |
| | | N(1)-C(2)-N(2) | 106.9(4) |

Scheme 1

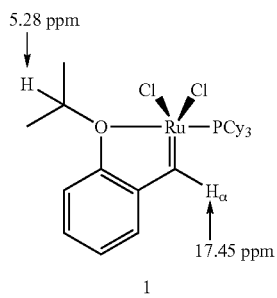

Synthesis of Formula 5. The catalyst of Formula 5 was synthesized and characterized, and its reactivity and recyclability were determined. It was determined that the saturated

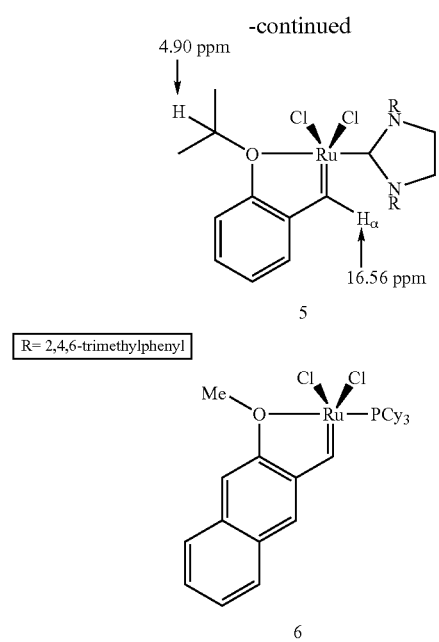

Catalytic Activity and Recovery of Formula 5 catalyst. The data in Table 2 below illustrate that the Formula 5 catalyst is an effective catalyst for RCM of dienes. In this reaction, hetero- and carbocyclic compounds bearing trisubstituted alkenes were obtained from the corresponding precursor dienes in the presence of 5 mol % catalyst at ambient temperature within 10 min. to 2 h. As shown in entries 1 and 2 of Table 2, both 1,1-disubstituted (7) and trisubstituted olefins (9) may be utilized in the synthesis of trisubstituted cyclic alkenes. The catalytic RCM in entries 3-4 indicate that trisubstituted allylic alcohols (12) and acetates (14) can be accessed in the presence of 5 mol % 5 within 2 h. The Ru catalyst of Formula 5 is recovered with high efficiency (95% and >98% yield, respectively). The prior art catalyst 1 is significantly less efficient in promoting the above transformations. As an example, treatment of structure 11 with 5 mol % 1 (22° C., $CH_2Cl_2$) leads to only 15% conversion after 2 h (as judged by 400 MHz $^1$H NMR).

Two important points in connection to the above data are important:

(1) In all instances, the catalyst is recovered, along with the desired cyclic product in high yield after simple silica gel chromatography. Moreover, addition of 2 equivalents of styrene ether 4 (relative to the catalyst) to a solution of a transformation promoted by the non-recyclable 3 at the end of the reaction time, leads to the isolation of the recyclable catalyst 5. As an example: Treatment of diene carbinol 11 is treated with 5 mol % 3 ($CH_2Cl_2$, 22° C., 1 h), followed by the addition of 10 mol % 4 and addition stirring for 1 h, leads to the formation of 12 and 5 in 98% and 82% yields, respectively (after silica gel chromatography).

(2) Catalyst loading lower than 5 mol % is sufficient. As exemplified by the reaction in entry 2, catalytic RCM can readily proceed to completion with only 1 mol % Formula 5 catalyst. As another example, catalytic RCM of 7 occurs within 10 mm at 22° C. in the presence of 1 mol % of 5 to afford 8 in 73% isolated yield (>98% conv); recovered 5 is obtained in 92% yield after chromatography.

As the reaction in entry 5 of Table 2 indicates, tetra-substituted olefins can also be obtained through catalytic RCM promoted by the catalyst of Formula 5.

TABLE 2

Ring-Closing Metathesis of Acyclic Dienes by Ru Complex 5[a]

| entry | substrate | product | time | conv (%) | product yield (%)[b] | catalyst recovery (%)[b] |
|---|---|---|---|---|---|---|
| 1 | 7 | 8 | 10 min | >98 | 82 | 98 |
| 2 | 9 | 10 | 20 min | >98 | 87 | 98 |

TABLE 2-continued

Ring-Closing Metathesis of Acyclic Dienes by Ru Complex 5[a]

| entry | substrate | product | time | conv (%) | product yield (%)[b] | catalyst recovery (%)[b] |
|---|---|---|---|---|---|---|
| 3 | 11 (OH) | 12 (OH) | 2 h | >98 | 75 | 95 |
| 4 | 13 (OAc) | 14 (OAc) | 1.5 h | >98 | 82 | >98 |
| 5 | 15 | 16 | 44 h | 42 | 38 | 81 |
| 6 | 17 | 18 | 30 min | 70 | 65 | 60 |

[a]Conditions: 5 mol % 5 for entries 1 and 3-6, 1 mol % 5 for entry 2, 22° C., CH$_2$Cl$_2$ (entries 1-4); 24 h at 22° C. and 20 h at 40° C., CH$_2$Cl$_2$ for entry 5; toluene, 80° C. for entry 6.
[b]Isolated yields after silica gel chromatography.

In this instance, the Ru catalyst is recovered in >80% yield. When toluene is used as the solvent in the catalytic RCM of compound 17, tetrasubstituted alkene 18 is formed in 65% isolated yield within 30 minutes (70% conversion).

The catalysts used the above-described transformations may be retrieved from the reaction mixture, e.g., using silica gel chromatography, and then may be used in subsequent metathesis reactions with equal efficiency and without recrystallization. For example, the catalyst recovered from the reaction in entry 1 of Table 2 was reused in the same reaction to afford the desired product 8 in 71% isolated yield (10 minutes, 22° C.). The Formula 5 catalyst was again recovered in 98% yield after chromatography.

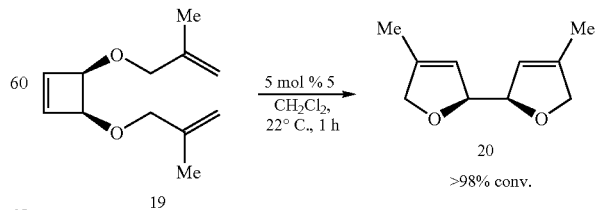

Scheme 2

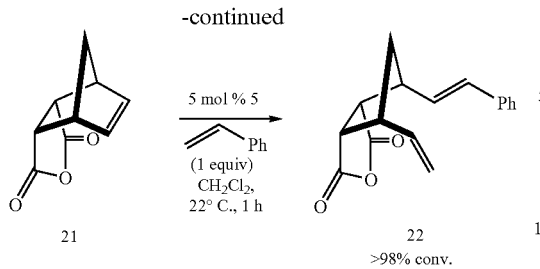

As shown by the representative transformations in Scheme 2, Formula 5 also is an efficient catalyst in ROM/RCM and ROM/CM processes. Both transformations were completed within 1 hour, with >98% conversion.

Scheme 3 shows the release/return mechanism by which the present monomeric catalysts function as metathesis catalysts. As shown therein, a diene substrate probably first reacts with the initial Ru complex to remove the transition metal from the styrene ligand and "release" the styrene ether 4. Upon consumption of the diene, the active Ru-carbene reacts with the previously occupied styrenyl ether to cause reformation or "return" of the initial complex.

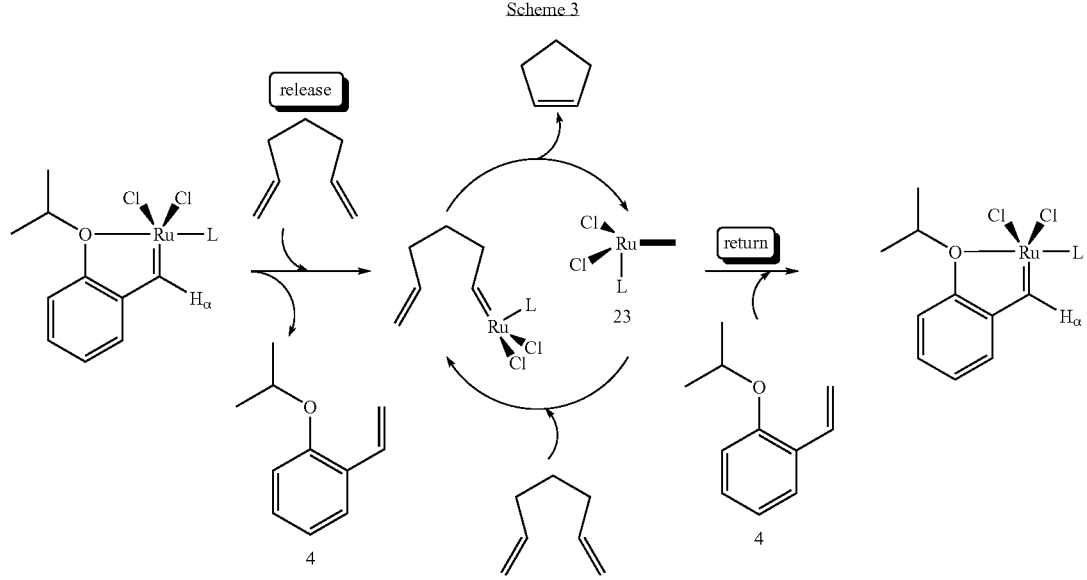

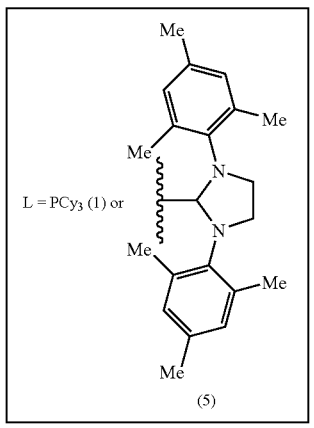

Dendritic complexes. In another aspect, the present invention provides dendritic catalysts having the structure shown as Formula III. Dendritic catalysts having Formula III can be prepared according the procedures described below, in Examples 11-16, or via other synthetic routes that would be readily ascertainable to these skilled in the art.

The structures shown as Formulae 30 and 31 below comprise currently preferred embodiments of the present invention.

Dendritic complexes, due to their different polarity compared to the monomeric species, generally can be more easily separated from reaction products. With dendrimers, it is possible to gauge more rigorously the efficiency with which the active metal-carbene leaves the ligation site and returns to the catalyst macromolecule. In addition both the release of the metal center from the styrenyl ligand (initiation) and the return of the active metal to the initial site (recovery), which is shown in Scheme 3 above, are more efficient with the more accessible and exposed terminal sites within the dendrimer structure.

Synthesis of Ru-Containing Dendrimers. In a currently preferred embodiment, the dendrimers are tetraalkylsilyl systems. Scheme 4 below shows a synthetic scheme for synthesizing a preferred Ru-containing dendrimer (Formula 30).

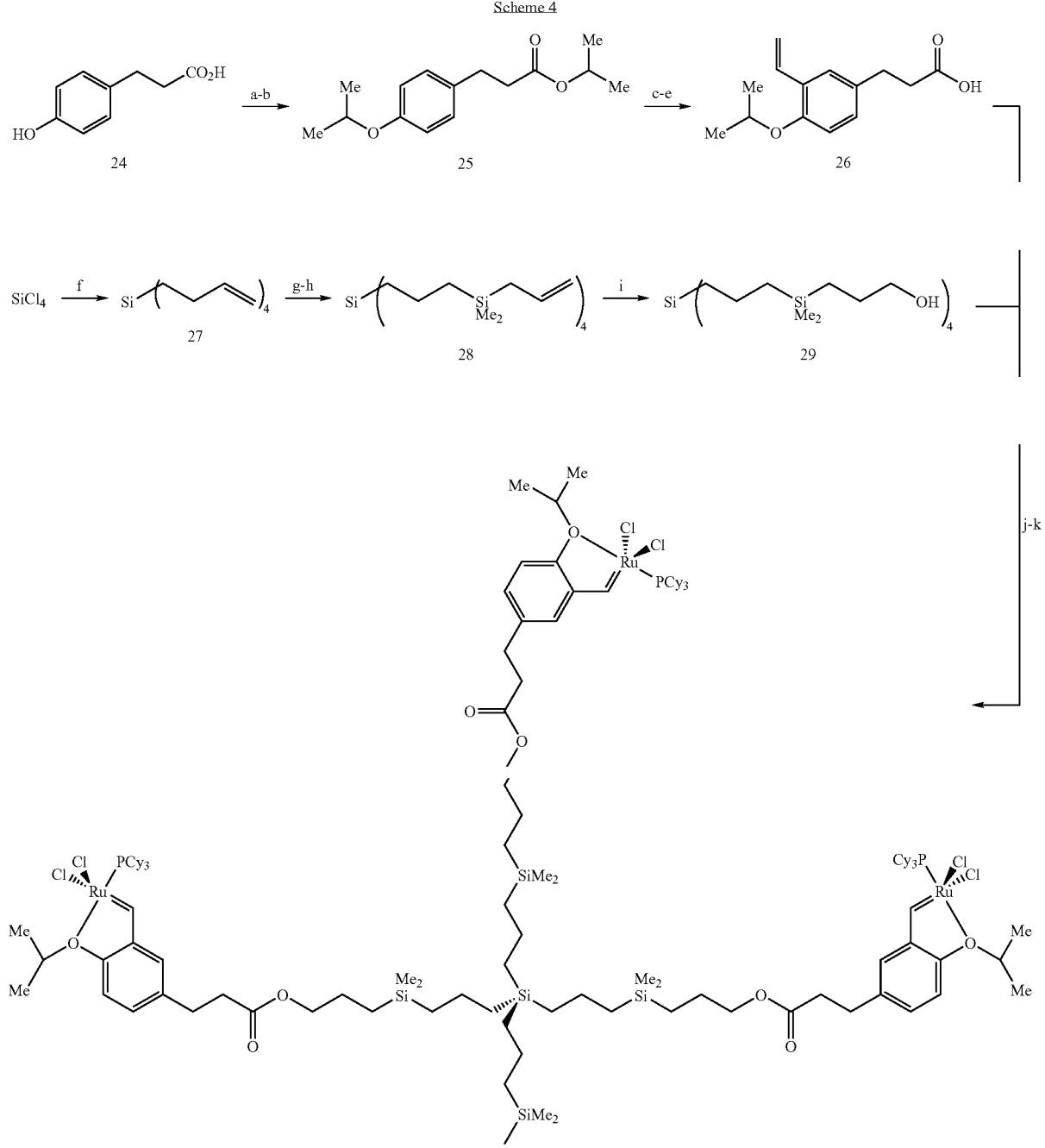

-continued

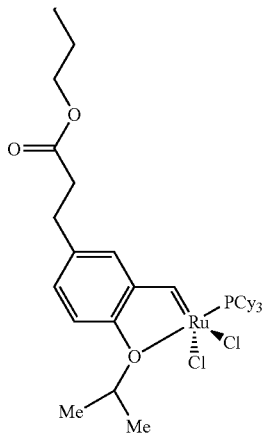

30 a. anhydrous HCl, i-PrOH, >87%, b, 2 equiv NaH, 2 equiv i-PrI, DMF, THF, 89%. c. 1.1 equiv $Br_2$, HOAc, $CH_2Cl_2$, 98%. d. 1.1 equiv $Bu_3SnCHCH_2$, 3 mol % $Pd(PPh_3)_4$, 2 mol % BHT, tol, 110° C., 4 h, >98%. g. 4.3 equiv $HMe_2SiCl$, 5 mol % $H_2PtCl_6$ in THF, 3 h. h. 4.2 equiv $CH_2CHCH_2MgBr$, $Et_2O$, 22° C., 3 h, >90% overall for two steps. i. 5.1 equiv 9-BBN, THF, 22° C., 17H; NaOH, $H_2O_2$, EtOH, THF, 22° C., 6 h, 96%. J. 4.9 equiv EDC-HCl, 4.5 equiv 26, 0.6 equiv DMAP, 22° C., 3 h, 63%. k. 4.3 equiv 2, 4.6 equiv CuCl, $CH_2Cl_2$, 22° C., 3 h, 83%.

The key features of the synthesis shown in Scheme 4 include the attachment of the requisite vinyl group through a pallidium (Pd)-catalyzed Stille coupling (→26) and preparation of the dendrimer backbone by a platinum (Pt)-catalyzed hydrosilation/alkylation/hydroboration sequence (27→28→29). Coupling of 29 with four equiv 26, followed by incorporation of the Ru center through treatment with 2 in the presence of CuCl affords the desired 30 as an air stable brown solid (mp=92-98° C. dec.).

Another preferred Ru-containing dendrimer, Formula 31, can be prepared as an air stable dark green solid by the same sequence of reactions as shown in Scheme 4, except that the last step involves treatment of the vacant dendritic structure with 4.3 equiv 3 and 4.6 equiv CuCl in $CH_2Cl_2$ for 10 mm (55% yield; mp=114-117° C. dec).

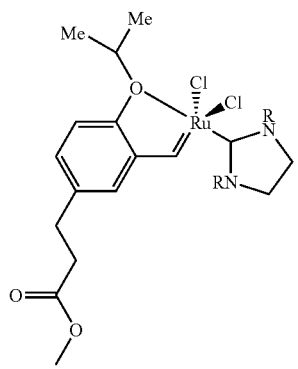

-continued

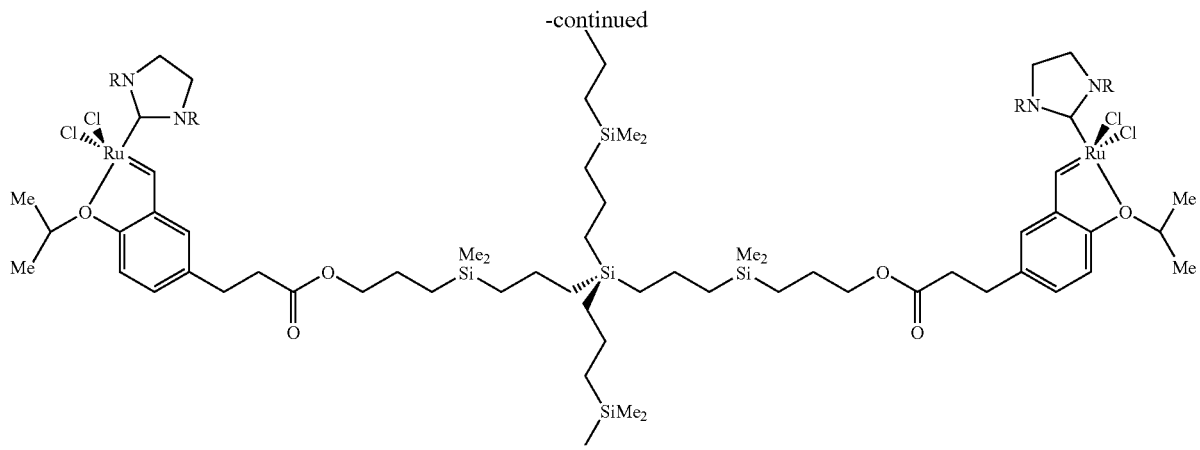

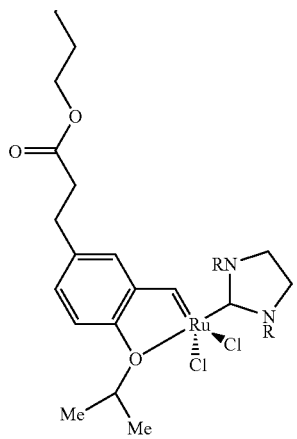

R = 2,4,6-trimethylphenyl

Catalytic RCM, ROM and CM Promoted by Dendritic Catalysts of Formulas 30 and 31. Table 3 below illustrates the use of the present dendritic catalysts in a RCM reaction. As shown in Table 3, treatment of diene 32 with 1.25 mol % of 30 (5 mol % Ru) leads to efficient and catalytic RCM. The desired product (33) is first isolated in 99% yield by silica gel chromatography through elution with $CH_2Cl_2$ subsequent wash of the silica with $Et_2O$ leads to the isolation of the dendritic catalyst (>98% mass balance). Recovered 30 was analyzed by 400 MHz $^1H$ NMR spectroscopy; the resulting spectrum indicated that 13% of the styrenyl ligands were vacant (approximately 13% Ru loss).

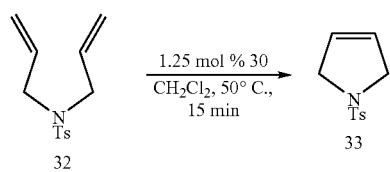

TABLE 3

Utility of Dendritic Catalyst Formula 30 in Catalyzing RCM

| Cycle | product yield[a] (%) | Ru content[b] (%) |
|---|---|---|
| 1 | 99 | 87 |
| 2 | 91 | 76 |
| 3 | 96 | 72 |
| 4 | 89 | 64 |
| 5 | 92 | 48 |
| 6 | 87 | 41 |

[a]Isolated yields after silica gel chromatography.
[b]Determined by analysis of the 400 MHz $^1H$ NMR of the purified reaction mixture of dendrimer after silica gel purification (devoid of other Ru-containing impurities).

As illustrated in Table 3, repeated use of Formula 30 as a catalyst results in complete conversion of 32 to 33 and isolation of the desired product in >86% isolated yield. These data thus illustrate that dendrimer 30 is effective in promoting the catalytic RCM of terminal dienes in a highly efficient manner, and can be easily recovered by simple silica gel filtration and reused repeatedly in subsequent reactions. In addition, after repeated use, the partially depleted dendrimer complex can be easily re-metalated upon treatment with the appropriate equivalents of 3 and CuCl in $CH_2Cl_2$. The dendritic complex remains active even after nearly 50% of the Ru content has been depleted (see cycle 6 in Table 3). This level of reactivity may be attributed, at least partially, to the fact that 30 (similar to monomeric catalysts 1 and 5) releases a highly active mono-phosphine Ru complex into the solution. In the absence of a second equivalent of $PCy_3$ that can re-coordinate to Ru and retard its catalytic activity (which is the case when 2 or 3 are used as catalysts), and since styrene ethers probably do not kinetically re-associate with Ru as efficiently as $PCy_3$, even a small amount of Ru release can lead to substantial amounts of metathesis activity.

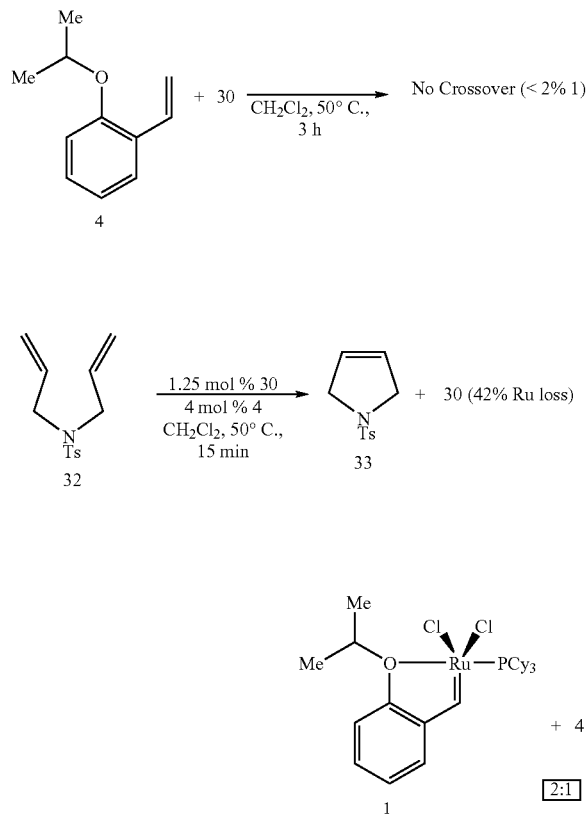

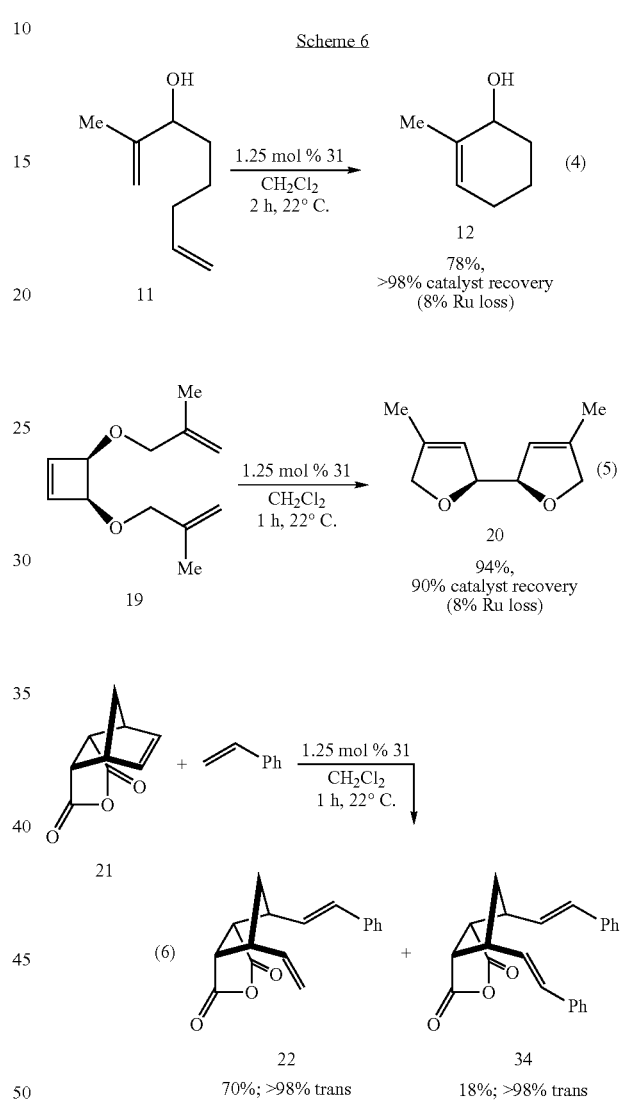

meric styrenyl alkoxide is recovered as monomeric Ru complex 1. These observations indicate that the Ru metal, after reacting with the diene substrate and leaving the dendrimer, can be trapped again by a styrenyl alkoxide. Thus, in the absence of compound 4, the catalytically active Ru monophosphine would likely return to a styrene unit within the dendritic structure.

Metal crossover experiments were carried out as depicted in Scheme 5. Treatment of compound 4 with dendritic Ru complex of Formula 30 results in little or no metal crossover (<2% 1 formed by 400 MHz 1H NMR analysis). The amount of Ru bound to the dendritic vs monomeric ligands is readily determined by the chemical shift difference in the $^1H$ NMR spectra of the corresponding carbene CH (Ru═C(H)). When diene substrate 32 is treated with 1.25 mol % fully loaded 30 and 4 mol % 4, RCM product 33 is obtained within 15 mm. However, recovered 30 bears 42% less Ru, compared to 13% metal reduction when the reaction is carried out in the absence of 4 (see Table 3, cycle 1). In addition, ~30% of uncomplexed 4 is isolated after the reaction; the remainder of the mono- Dendrimer 31 exhibits catalytic activity higher than that observed for 30. Unlike 1 or 30, but similar to 5, dendritic 31 efficiently promotes the formation of trisubstituted allylic alcohol 12 (Scheme 4); in addition to the desired product (78%), the dendrimer is recovered after silica gel chromatography quantitatively with 8% loss in Ru loading (judged by analysis of 400 MHz $^1H$ NMR). Moreover, as shown in Equation (5), similar to 5, dendrimer 31 effectively catalyzes tandem ROM/RCM of 19 and the formation of 20 (94%). However, in contrast to the corresponding monomer 5, dendrimer 31 can be easily separated from 20 and recovered in 90% yield (8% Ru loss). The transformation in Scheme 6 indicates that 31 effectively promotes catalytic ROM/CM reactions as well, and as before, it can be recovered readily and in good yield (>98% trans olefins in 22 and 34, as judged by 400 MHz $^1$H NMR analysis). Thus, dendritic catalyst 31 retains the high activity of monomeric 5 and provides the valuable practical advantage of being readily separable from metathesis products.

Similar to monomeric 5, lower loadings of 31 are sufficient for efficient catalytic metathesis. As an example, when triene 7 is treated with 0.25 mol % 31 (CH$_2$Cl$_2$, 22° C.) for 10 min, RCM adduct 8 is formed with >98% conv. In addition to dihydrofuran 8, isolated in 84% yield, recovered 31 is obtained in 88% yield after silica gel chromatography (22% Ru loss).

Immobilization of the Catalysts on a Solid Phase. The present catalysts can be attached to or immobilized on a solid support for use in metathesis reactions. Solid phases which can be used include, for example, metals (including magnetic media), glass, polymers, ceramics or other inert substances that will not affect the reaction. The solid phase may be in any form useful for carrying out the particular reaction, including particles, beads, rods, plates, fibers, filters, etc. Methods for attaching organometallic catalysts to solid supports and using them in metathesis reactions are known in the art. One method for attaching the preferred monomeric catalyst of the present invention to a polymer substrate is described in Example 19.

The catalysts of the present invention can be immobilized with retention of all the ligand environment characteristics responsible for its high activity. In one embodiment, the immobilized catalyst is immobilized on the solid support in a manner such that the support is a catalyst carrier. In this embodiment, the metathesis substrate releases the active metal carbene from the polymer, the complex promotes several cycles in solution, and is again trapped by the support so that it can be easily retrieved and reused. In other words, the present immobilized catalyst systems combine the benefits of heterogeneous catalysis (recyclability) and homogeneous catalysis (high turnover).

In a preferred embodiment of the invention, the transition metal catalysts are immobilized on solid phase surfaces such as, for example, metals, glass, polymers, ceramics, organic polymer beads, inorganic sol-gels and other inert substances, without impairing their ability to catalyze various forms of metathesis reactions in a highly efficient manner. In a currently preferred embodiment, the solid phase is an inorganic sol gel such as, for example, a glass monolithic gel.

The surface immobilization of the catalysts to solid phase substrates involves a preliminary step wherein the catalysts are chemically reacted with an organic coupling agent to provide adducts that are capable of chemically bonding to said solid phase substrates. In a preferred embodiment, the said adduct contains a silyl functionality that enables surface immobilization on solid phase substrates via chemical bonding of the silyl group to the said substrates. In a most preferred embodiment the catalysts of the invention are coupled to the organic linker and functionalized with a silane-containing moiety in a single step. Surface immobilization of the said silane modified compounds onto solid phase substrates is accomplished in-situ by subsequent addition of said substrate into the reaction vessel. Preferred coupling agents are norbornene derivatives that are capable of reacting with catalysts of the invention, and further capable of reacting with organosilane agents to provide silyl-functionalized derivatives that may be used in surface immobilization reactions. Preferred solid phase substrates include those capable of chemically reacting with the silyl moiety. In a most preferred embodiment, the solid phase substrate is a porous glass monolith having preferably an average pore size of about 200 Å. More specifically, as shown in Scheme 7, a ring-opening reaction combined with cross metathesis of anti-norbornenol ester 35 in with 1.0 equivalent each of organometallic complex 3 and allylchlorodimethylsilane (0.05 M CH$_2$Cl$_2$, 22° C.) proceeds to >98% conversion in <1 h to give adduct 36 (analyzed by 400 MHz $^1$H NMR). Surface immobilization of adduct 36 is accomplished by adding a pre-weighed batch of vacuum-dried sol-gel monoliths such as, for example, glass monolithic gel with about 200 Å pore size to the reaction mixture, followed by stirring for 96 h at 40° C. After extensive washing with CH$_2$Cl$_2$ and drying in vacuo, bright green glass pellets of surface immobilized catalyst 37 are recovered.

Figure 4:
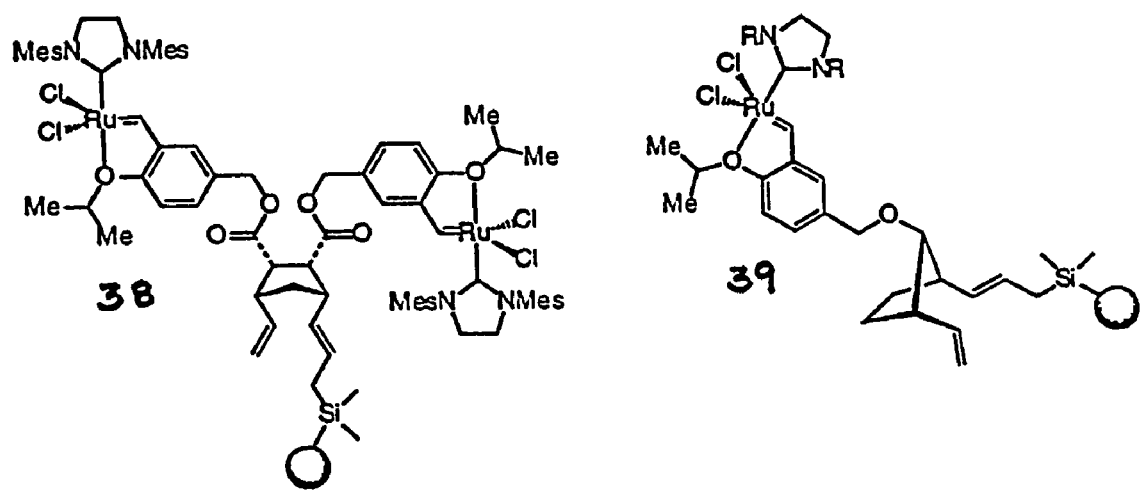
FIG. 4 shows surface immobilized catalysts of the invention coupled to a solid phase (represented by a spherical solid substrate) via different types of linkers.

In other preferred embodiments, surface immobilized catalysts 38 and 39 shown in FIG. 4 are obtained in an analogous fashion from the corresponding norbornene substrates. Surface immobilized catalysts 37, 38 and 39 were evaluated for catalytic activity, recovery and recyclability.

Scheme 7

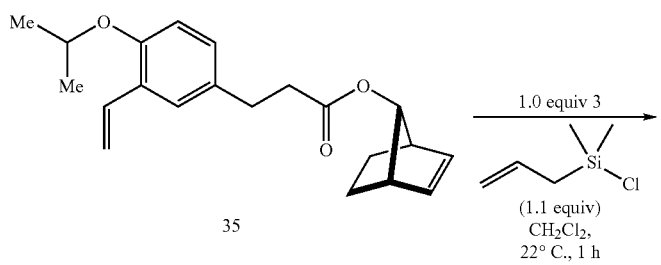

-continued

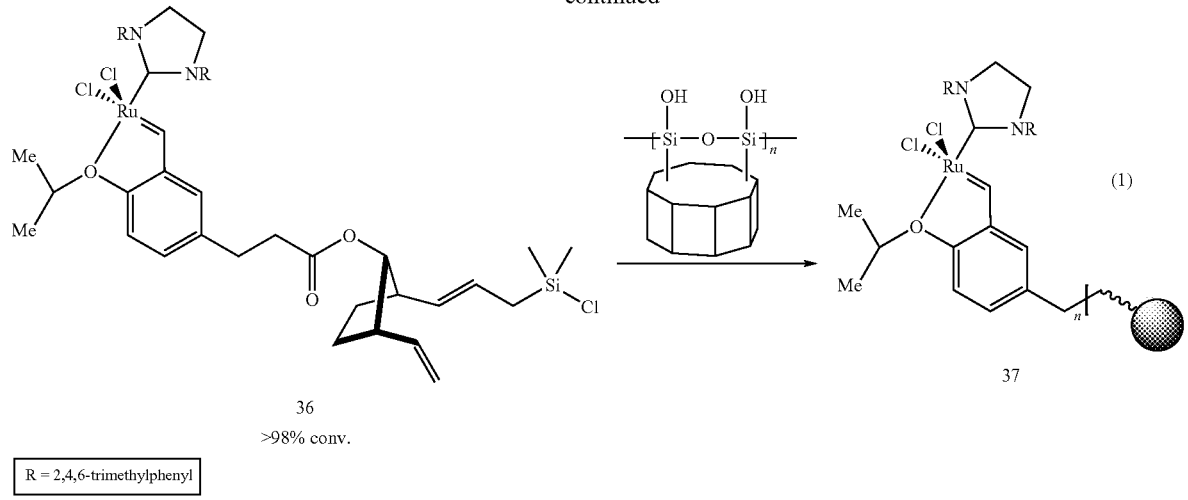

36
>98% conv.

R = 2,4,6-trimethylphenyl (1)

37

All surface immobilized catalysts of the present invention show good activity in catalyzing metathesis reactions. Table 4 shows efficiency of immobilized catalysts 37, 38 and 39 carried through iterative rounds of ring-closing metathesis (RCM) of acrylic amide 40 to yield 41. The catalyst lo:

that accompany functionalization of the gel surface. Relative reaction rates of three catalysts were assessed by stopping the reaction prematurely during the third round of RCM, at a point where TLC analysis still showed the presence of a small amount of starting material. Spectroscopic analysis of the (400 MHz $^1$H NMR) unpurified reaction mixture (97-100% conversion, Round 3, Table 4) indicates that reaction efficiency of all three catalysts tested are equivalent.

Figure 3:
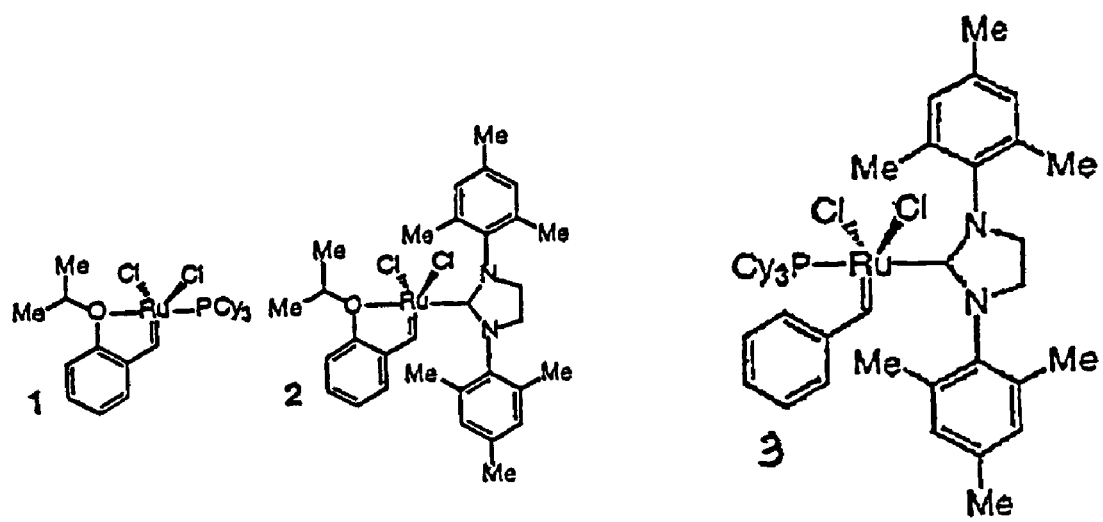
FIG. 3 shows the transition metal catalysts (1, 2) and organometallic compound 3 comprising an active metal complex.

The surface immobilized catalysts of the present invention provide the following advantages over non-immobilized catalysts 1 and 2 and 3 (FIG. 3).

(1) In contrast to reactions run with 5 mol % non-immobilized catalysts 1 and 2, the proton NMR spectra of the unpurified reaction mixtures in every case consists of >98% pure cyclo-olefin (analyzed by 400 MHz $^1$H NMR); no catalyst or byproduct thereof is detected). Concentration of the reaction mixtures consistently deliver the cyclo-olefins as an off-white solids in >98% yield. These materials meet the acceptance criteria as defined by CH combustion analysis without need for purification.

(2) No post reaction filtration step is required for product isolation and catalyst recovery. The reaction mixture is removed by pipetting, decantation or pumping, following which the solid surface (for example, inorganic gel pellets such as glass) with the immobilized catalyst is washed with $CH_2Cl_2$, prior to addition of fresh substrate for a subsequent metathesis reaction.

(3) After four consecutive rounds of RCM utilizing surface immobilized catalysts with different organic linker types, the respective gel pellets after thorough drying in vacuo and subsequent weighing yielded mass differences that are highly reproducible, indicating a net metal loss of between 20 to 25% over the four reaction cycles. Despite this significant drop in Ru catalyst loading relative to the initial values, the catalytic activities of the recovered, recycled gel pellets remain high. Absence of cross-contamination of reaction products by surface immobilized catalysts of the present invention may be demonstrated by using the same samples for the ring-opening metathesis (ROM) of 7-anti-norbornenol in the presence of a variety of donor olefins, including highly electron-rich olefins such as vinylferrocene. As shown in Table 5, productive metathesis for three additional rounds of norbornenol 42 occurred in <1 h to yield ring-opened compound 43. The Ru-containing impurities, as well as the product of the previous RCM reaction 41 could not be detected by

TABLE 4

Utility of Immobilized Catalysts in catalyzing RCM

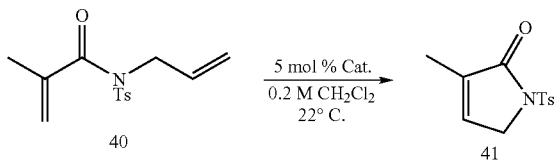

| Catalyst | Round 1 (3 h) | Round 2 (3 h) | Round 3 (2 h) | Round 4 (3 h) | Metal Loss |
|---|---|---|---|---|---|
| 37 | >98% conv, 99% | >98% conv, 100% | 97% conv, 100% | >98% conv, 99% | 1.8 mg (25%) |
| 38 | >98% conv, 100% | >98% conv, 100% | 97% conv, 99% | >98% conv, 100% | 1.9 mg (20%) |
| 39 | >98% conv, 99% | >98% conv, 99% | 99% conv, 100% | >98% conv, 100% | 1.6 mg (22%) |

NMR spectroscopy (400 MHz $^1$H NMR analysis) of the corresponding unpurified reaction product mixtures.

TABLE 5

Efficiency of Recycled Catalysts in catalyzing ROCM

[Scheme: compound 42 (norbornene with HO group) + CH$_2$=CHR (1.0 equiv), 5 mol % Cat., 0.2 M CH$_2$Cl$_2$, 22° C. → compound 43]

| Catalyst | R = Ph Rounds 5 (40 min) | R = n-hexyl Round 5 (40 min) | R – Ferrocene Round 7 (40 min) |
|---|---|---|---|
| 37 | >98% conv | >98% conv | >98% conv |
| 38 | >98% conv | >98% conv | >98% conv |
| 39 | >98% conv | >98% conv | >98% conv |

In addition to attaching the catalyst to a substrate such as an organic polymer bead that necessitates an additional filtration step to isolate the product from catalyst, the catalysts of the invention may be immobilized on the surface of a reaction vessel. In a preferred embodiment, the catalyst metal complex is immobilized to an integral part of the reaction apparatus itself, for example, a glass round-bottom reaction flask, a magnetic stir bar, or other component used to carry out the reaction. Catalysts of the present invention may also be attached to highly porous glass monoliths, which can be synthesized and manipulated from readily available materials.

Preferably, the linker moiety used to bind the metal complex to the solid support should be chemically inert under the reaction conditions and form a non-labile link between the metal complex and support. In one embodiment, as shown in Scheme 7, the present catalysts are immobilized using a procedure that allows incorporation of both the linker and the active metal complex in a single step. Subsequent diffusion of the catalyst and linker into the pores of a sol gel material, for example, results in a substitution reaction involving the labile Si—Cl bond with free hydroxyl groups on the glass surface, thereby immobilizing the catalyst to the glass surface.

As shown in Example 19, ring-opening cross metathesis (0.10 mmol scale) of a strained olefin using the catalyst synthesized according to Example 4 (shown as Formula 3 in Equation 1 above) proceeded to >98% conversion. In this reaction, a catalyst of the present invention was immobilized on a single 50 mg sol gel monolith. After extensive washing and drying in vacuo, a bright green glass pellet was recovered which showed good activity in the RCM of the terminal diene (0.10 mmol scale). The immobilized catalyst was carried through three iterative rounds of metathesis.

The following Examples are provided to illustrate the present invention, and are not intended to be limiting in any way.

EXAMPLES

General. Infrared (IR) spectra were recorded on a Perkin-Elmer 781 spectrophotometer, λmax in cm$^{-1}$. Bands are characterized as broad (br), strong (s), medium (m), and weak (w). $^1$H NMR spectra were recorded on Varian Unity 300 (300 MHz), Gemini 2000 (400 MHz), or INOVA 500 (500 MHz) spectrometers. Chemical shifts are reported in ppm from tetramethylsilane with the solvent resonance as the internal standard (CDCl$_3$): δ7.26 ppm; CD$_3$CN: δ 1.94 ppm). Data are reported as follows: chemical shift, multiplicity (s=singlet, d=doublet, t=triplet, br=broad, m multiplet), coupling constants (Hz), integration, and assignment. $^{13}$C NMR spectra were recorded on Varian Unity 300 (75 MHz), Gemini 2000 (100 MHz), or INOVA 500 (125 MHz) spectrometers with complete proton decoupling. Chemical shifts are reported in ppm from tetramethylsilane with the solvent as the internal reference (CDCl$_3$: 77.00 ppm; CD$_3$CN: 1.19 ppm). $^{31}$P NMR spectra were recorded on a Varian Gemini 2000 (162 MHz) spectrometer with complete proton decoupling. The chemical shifts of the phosphorus resonances were determined relative to phosphoric acid as an external standard (H$_3$PO$_4$: δ 0.0 ppm).

All reactions were carried out under an atmosphere of dry Ar in oven—(135° C.) and flame-dried glassware with standard Schlenk or vacuum-line techniques. In most instances, solid organometallic compounds were purified and recovered in air and later stored in a drybox under an atmosphere of argon. (PCy$_3$)Cl$_2$RuCHPh (Formula 2) was prepared according to literature procedures.[30] (4,5-dihydroIMES)(PCy$_3$)Cl$_2$Ru=CHPh (Formula 3) and its requisite starting materials were prepared by a modification of the published method[31] (see below for further details). 2-isopropoxystyrene was prepared by alkylation and Wittig olefination. All other materials were obtained from commercial sources and purified before use. Tetrahydrofuran, diethyl ether, benzene, and toluene were distilled from sodium metal/benzophenone ketyl. Dichloromethane, pentane, hexanes, 2-propanol, triethylamine, and ethanol were distilled from calcium hydride under Ar. Methanol was distilled over Mg under Ar. 2,4,6-trimethylaniline was vacuum distilled. Triethyl orthoformate (Aldrich) was distilled from MgSO$_4$ under reduced pressure. 3-(4-Hydroxyphenyl)-propionic acid (Aldrich) was recrystallized from water. 2-Iodopropane (Aldrich) was distilled from MgSO$_4$ under argon. Dimethylformamide (Fisher) was stored over 4A molecular sieves prior to use. Tributyl(vinyl)tin (Aldrich) was vacuum distilled from MgSO$_4$. Allylmagnesium bromide was freshly prepared from distilled allyl bromide (Aldrich) and Mg turnings (Strem) and titrated before use. Silicon tetrachloride (Strem) was distilled under argon. Chlorodimethylsilane (Aldrich) was distilled under argon. 9-Borabicyclo[3.3.1]nonane (9-BBN) was freshly prepared from distilled 1,5-cyclooctadiene (Aldrich), borane-dimethylsulfide complex (Aldrich), and anhydrous dimethoxyethane (Aldrich, distilled from sodium metal/benzophenone ketyl).[32] 4-Dimethylaminopyridine (DMAP) (Aldrich) was recrystallized from anhydrous toluene. The following materials were purchased from commercial sources and used as received: glyoxal (40% wt. soln in water)(Aldrich), sodium cyanoborohydride (Aldrich), bromocresol green (Fisher), ammonium tetrafluoroborate (Aldrich), potassium tert-butoxide (Strem), copper(I) chloride (Strem), anhydrous HCl (Aldrich), sodium hydride (Aldrich), bromine (Aldrich), acetic acid (Fisher), sodium thiosulfate (Aldrich), 2,6-di-tert-butyl-4-methylphenol (Aldrich), tetrakis(triphenylphosphine)palladium (0)(Strem), activated carbon (Aldrich), chloroplatinic acid hexahydrate (Speier's catalyst) (Strem), platinum-divinyltetramethylsiloxane complex in xylene (Karstedt's catalyst)(Geleste), hydrogen peroxide (30% wt. soln in water)(Aldrich), citric acid (Aldrich), and 1-(3-dimethylaminopropyl)-3-ethyl carbodiimide (EDC) (Advanced Chemtech).

All silica gel column chromatography was driven with compressed air and performed with silica gel 60 (230-400 mesh; pH (10% suspension) 6.5-7; surface area 500 m$^2$/g; pore volume 0.75 ml/g) obtained from TSI Chemical Co. (Cambridge, Mass.). Similar to the original monomer 1, dendritic catalyst 30 forms a dark brown solution in organic solvents. In contrast, the more active catalysts bearing the 4,5-dihydroIMES ligand form bright green-colored organic solutions. The purification of the above complexes can be easily monitored visually since they appear as dark brown or green-colored bands on the column. Dendritic complexes 30 and 31 are significantly more polar than the corresponding monomers. Following a metathesis reaction mediated by 30 or 31, isolation of both product and catalyst typically involved simply a filtration of the crude mixture through a silica gel plug in 100% $CH_2Cl_2$ followed by a column "flush" in 100% $Et_2O$ (TLC Rf of 30 and 31<1.0 in $CH_2Cl_2$).

Example 1

Synthesis of ((2,4,6-Trimethylphenyl)NCH)$_2$

Glyoxal (3.73 mL of a 40% weight solution in water, 32.5 mmol) was dissolved in 325 mL of reagent-grade methanol in a 500 mL flask. 2,4,6-Trimethylaniline (8.25 mL, 58.8 mmol, 1.81 equiv) was added dropwise to this solution by syringe. The mixture was stirred for 12 h at 22° C. as a bright yellow precipitate slowly formed. The mixture was diluted with $CH_2Cl_2$, dissolving the solid. The resulting yellow solution was dried over $MgSO_4$, filtered, and concentrated to a yellow-orange solid residue. The unpurified product was recrystallized from anhydrous methanol (for every 10 g, 850-900 mL of MeOH was required for complete dissolution at reflux). After slow cooling to 22 EC followed by subsequent storage of the sample at −20° C. for 12 h, long canary yellow crystals formed. The product was recovered by vacuum filtration, washed with pentane, and dried under high vacuum (7.40 g, 25.3 mmol, 86%). IR (NaCl): 3005 (m), 2946 (s), 2916 (s), 2854 (m), 2725 (w), 1617 (s), 1595 (w), 1476 (m), 1438 (w), 1374 (m), 1265 (m), 1202 (s), 1141 (m), 1031 (w), 850 (s), 780 (m), 739 (s), 705 (w), 609 (w). $^1$H NMR (400 MHz, $CDCl_3$): 8.12 (s, 2H, NCH), 6.93 (s, 4H, aromatic CH), 2.31 (s, 6H, mesityl p-$CH_3$), 2.18 (s, 12H, mesityl o-$CH_3$). $^{13}$C NMR (100 MHz, $CDCl_3$): δ163.31, 147.29, 134.13, 128.86, 126.44, 20.83, 18.28. HRMS Calcd for $C_{20}H_{23}N_2$: 292.1861 (M−H)$^+$. Found: 291.1862. Anal. Calcd for $C_{20}H_{24}N_2$: C, 82.15; H, 8.27. Found: C, 81.99; H, 8.12.

Example 2

Synthesis of ((2,4,6-Trimethylphenyl)NHCH$_2$)$_2$

The bis(imine)((2,4,6-trimethylphenyl)NCH)(7.30 g, 25.0 mmol) was suspended in 250 mL of MeOH in a 500 mL round-bottom flask. Several crystals of bromocresol green were added as a pH indicator and the mixture was cooled to 0° C. $NaCNBH_3$ (10.0 g, 159 mmol, 6.4 equiv) was added to the reaction mixture in one portion as a solid. Vigorous bubbling was observed and the reaction mixture turned a deep blue-green color (alkaline pH). After 10 mm concentrated HCl was added dropwise to the mixture, restoring its original yellow color. Additional reduction slowly occurred, causing the mixture to again become basic. The acidification process was repeated (typically two more times) until the yellow color persisted. The reaction mixture was warmed to 22° C. and stirred for 1 h. A solution of 2 M KOH was added dropwise until the mixture was weakly alkaline (pH=8-9). The mixture was then diluted with water (300 mL), transferred to a separatory funnel, and washed three times with $Et_2O$ (500 mL). The combined organic layers were washed with 800 mL of saturated solution of sodium chloride, dried over $MgSO_4$, filtered, and concentrated into a yellow oil. Silica gel chromatography (TLC Rf=0.32 in 4:1 pentane: $Et_2O$) afforded the product as a colorless oil (7.13 g, 24.1 mmol, 96%). IR (NaCl): 3367 (br), 2996 (s), 2916 (s), 2854 (s), 2729 (w), 1612 (w), 1485 (s), 1446 (s), 1373 (m), 1344 (w), 1228 (s), 1207 (m), 1154 (m), 1110 (m), 1062 (w), 1030 (m), 1012 (m), 853 (s), 822 (w), 801 (w), 738 (m), 563 (m). $^1$H NMR (400 MHz, $CDCl_3$): δ 6.85 (s, 4H, aromatic CH), 3.30 (br, 21-1, NH), 3.17 (s, 4H, $NCH_2CH_2N$), 2.30 (s, 12H, mesityl o-$CH_3$), 2.25 (s, 6H, mesitylp-$CH_3$). $^{13}$C NMR (100 MHz, $CDCl_3$): δ 143.24, 131.35, 129.65, 129.38, 49.19, 20.60, 18.50. HRMS Calcd for $C_{20}H_{28}N_2$: 296.2252 Found: 296.2258. Anal. Calcd for $C_{20}H_{28}N_2$: C, 81.03; H, 9.52. Found: C, 81.28; H, 9.41.

Example 3

Synthesis of 1,3-Dimesitylimidazolinium Tetrafluoroborate

A 25 mL round-bottom flask was charged with ((2,4,6-trimethylphenyl)NHCH$_2$)$_2$ (7.81 g, 26.4 mmol) and ammonium tetrafluoroborate (2.77 g, 26.4 mmol, 1.0 equiv). Triethylorthoformate (4.39 mL, 26.4 mmol, 1.0 equiv) was added by syringe. The flask was equipped with a reflux condenser and submerged into a preheated oil bath at 120° C. The mixture was refluxed for 3 h and cooled to 22° C. A tan-colored solid precipitated, leaving a cloudy suspension. This mixture was recrystallized from hot anhydrous ethanol. The resulting bright white crystals of product were recovered by vacuum filtration, washed with pentane, and dried under high vacuum (5.62 g, 14.3 mmol, 54%). Additional product could be obtained by further recrystallization of the mother liquor. IR (NaCl): 3091 (w), 2979 (br), 2941 (br), 1633 (s), 1487 (w), 1459 (w), 1393 (w), 1313 (w), 1269 (m), 1214 (w), 1092 (m), 1054 (s), 1036 (s), 965 (w), 880 (w), 852 (m). $^1$H NMR (400 MHz, $CD_3CN$): δ 8.14 (s, 1H, NCHN), 7.08 (s, 4H, aromatic CH), 4.43 (s, 4H, $NCH_2CH_2N$), 2.37 (s, 12H, mesityl o-$CH_3$), 2.32 (s, 6H, mesityl p-$CH_3$). $^{13}$C NMR (100 MHz, $CD_3CN$): δ 160.41 (d, $^JNC$=10.3 Hz), 141.54, 136.50, 131.36, 130.61, 52.21, 21.16, 17.92. HRMS Calcd for $C_{21}H_{27}N_2$: 307.2174 (cation only). Found: 307.2175. Anal. Calcd for $C_{21}H_{27}BF_4N_2$: C, 63.97; H, 6.90. Found: C, 63.79; H, 6.85.

Example 4

Synthesis of (4,5-dihydroIMES)(PCy$_3$) $Cl_2Ru$=CHPh (formula 3)

The ligand salt 1,3-dimesitylimidazolinium tetrafluoroborate (2.94 g, 7.46 mmol, 1.2 equiv) was suspended in 50 mL of THF in a 250 mL round-bottom flask. This mixture was then treated with a solution of potassium tert-butoxide (840 mg, 7.49 mmol, 1.2 equiv) in 50 mL of THF via cannula at 22° C. This mixture was immediately cannula transferred (20 mL THF used as rinse) to a second vessel containing a solution of (PCy$_3$)$Cl_2Ru$=CHPh (2)(5.01 g, 6.09 mmol, 1.0 equiv) in 100 mL of benzene (additional stirring of the ligand salt mixture at 22° C. prior to exposure to the Ru-carbene often resulted in incomplete conversion to the desired product). The resulting mixture was refluxed at 80° C. for 30 min. and then cooled to 22° C. All manipulations from this point forward were carried out in air with reagent-grade solvents. The solvents were removed at reduced pressure, leaving a red-brown solid residue. The crude residue was dissolved in a minimal volume of 9:1 hexanes: $Et_2O$ and loaded onto a wide plug of silica gel. Elution with the same solvent system slowly removed a pink-red band of the desired product from the column. Concentration of the product fractions in vacuo removed the more polar and volatile Et$_2$O and resulted in spontaneous precipitation of the catalyst from hexanes as a cranberry red, microcrystalline solid (3.78 g, 4.45 mmol, 73%). These crystals were dried under high vacuum. IR (NaCl): 3057 (m), 3039 (m), 3015 (m), 2927 (s), 2850 (s), 1608 (w), 1479 (s), 1446 (s), 1421 (s), 1380 (m), 1328 (w), 1266 (s), 1243 (m), 1205 (w), 1174 (m), 1129 (w), 1036 (w), 1005 (m), 909 (m), 849 (m), 737 (s), 703 (m), 687 (m), 624 (w), 578 (w). $^1$H NMR (300 MHz, CDCl$_3$): δ 19.13 (s, 1H, Ru=CHAr), 7.35 (dd, J=7.8, 7.0 Hz, 2H, aromatic CH), 7.09 (m, 3H, aromatic CH), 7.01 (s, 4H, mesityl aromatic CH), 3.98 (s, 4H, N(CH$_2$)$_2$N), 2.80-0.70 (m, 33H, P(C$_6$H$_{11}$)$_3$), 2.31 (s, 12H, mesityl o-CH$_3$), 1.90 (s, 6H, mesitylp-CH$_3$). $^{13}$C NMR (75 MHz, CDCl$_3$): δ 293.40, 220.29 (d, $^J$CN=76.2 Hz), 151.16, 151.11, 138.27, 137.49, 137.08, 135.06, 129.77, 127.78, 51.64 (d, $^J$CN=71.9 Hz), 31.30 (d, $^J$PC=15.6 Hz), 27.68 (d, =9.8 Hz), 26.07, 21.09, 20.86, 19.88. $^{31}$P NMR (162 MHz, CDCl$_3$): δ 161.90 (s, PCy$_3$). Anal. Calcd for C$_{46}$H$_{65}$Cl$_2$N$_2$PRu: C, 65.08; H, 7.72. Found: C, 65.18; H, 7.71.

Example 5

Synthesis of (4,5-dihydroIMES)Cl$_2$Ru=CH-o-O-i-Pr C$_6$H$_4$ (formula 5)

(4,5-dihydroIMES)(PCy$_3$)Cl$_2$Ru=CHPh (formula 3)(895 mg, 1.05 mmol, 1.03 equiv) and CÜCI (261 mg, 2.64 mmol, 2.59 equiv) were weighed into a 100 mL round-bottom flask in a glove box and dissolved in 20 mL of CH$_2$Cl$_2$. 2-isopropoxystyrene (4)(166 mg, 1.02 mmol, 1.0 equiv) was cannulated into the resulting deep red solution in 20 mL of CH$_2$Cl$_2$ at 22° C. The flask was equipped with a condenser and stirred at reflux for 1 h. From this point forth, all manipulations were carried out in air with reagent-grade solvents. The reaction mixture was concentrated in vacuo to a dark brown solid residue. The crude material was dissolved in a minimal volume of 2:1 pentane: CH$_2$Cl$_2$ and loaded onto a plug of silica gel. Elution with 2:1 pentane: CH$_2$Cl$_2$ and then 1:1 pentane: CH$_2$Cl$_2$ removed a bright green band from the column. The column was then washed successively with straight CH$_2$Cl$_2$ and Et$_2$O (light green/yellow bands elute). These three fractions were pooled and concentrated to a dark green solid. This material was passed through a second silica gel plug in 1:1 hexanes:CH$_2$Cl$_2$ (bright green band elutes). Subjection to reduced pressure removed the more volatile CH$_2$Cl$_2$ from the product solution and resulted in spontaneous precipitation of the catalyst from hexanes as a bright green crystalline solid; drying under high vacuum afforded 635 mg (1.01 mmol, 99%) of the desired product. IR (NaCl): 2922 (br), 2853 (m), 1730 (w), 1606 (w), 1589 (m), 1575 (w), 1478 (s), 1452 (s), 1420 (s), 1397 (m), 1384 (m), 1295 (m), 1263 (s), 1217 (m), 1160 (w), 1113 (s), 1098 (w), 1035 (w), 938 (m), 852 (w), 801 (w), 746 (m), 737 (m), 580 (m). $^1$H NMR (400 MHz, CDCl$_3$): δ 16.56 (s, 1H, Ru=CHAr), 7.48 (m, 1H, aromatic CH), 7.07 (s, 4H, mesityl aromatic CH), 6.93 (dd, J=7.4, 1.6 Hz, 1H, aromatic CH), 6.85 (dd, J=7.4, 7.0 Hz, 1H, aromatic CH), 6.79 (d, J=8.6 Hz, 1H, aromatic CH), 4.90 (septet, J=6.3 Hz, 1H, (CH$_3$)$_2$CHOAr), 4.18 (s, 4H, N(CH$_2$)$_2$N), 2.48 (s, 12H, mesityl o-CH$_3$), 2.40 (s, 6H, mesityl p-CH$_3$), 1.27 (d, J=5.9 Hz, 6H, (CH$_3$)$_2$CHOAr). $^{13}$C NMR (100 MHz, CDCl$_3$): 6296.83 (q, J=61.5 Hz), 211.13, 152.04, 145.13 (d, Joc=3.9 Hz), 145.09, 138.61, 129.39 (d, $^J$NC=3.9 Hz), 129.35, 129.17, 122.56, 122.11, 112.75, 74.86 (d, $^J$oc=10.7 Hz), 51.42, 30.86, 25.93, 21.08. HRMS Calcd for C$_{31}$H$_{38}$Cl$_2$N$_2$O$^{99}$ Ru: 623.1421 Found: 623.1411. Anal. Calcd for C$_{31}$H$_{38}$Cl$_2$N$_2$ORu: C, 59.42; H, 6.11; Cl, 11.32; N, 4.47. Found: C, 59.28; H, 6.35; Cl, 11.36; N, 4.12.

Example 6

Synthesis of Isopropyl-1-(p-hydroxyphenyl)propionate

Through a stirring solution of 3-(4-hydroxyphenyl) propionic acid (24)(5.00 g, 30.1 mmol) in 2-propanol (167 mL, 72.0 equiv) was bubbled anhydrous HCl for 50 mm. The flask was sealed under Ar and stirred for 12 h at 22° C. The solvent was removed under reduced pressure with gentle heating, leaving a thick, colorless oil. Removal of residual 2-propanol under high vacuum at 22° C. resulted in spontaneous precipitation of the desired product as a bright white crystalline solid (6.12 g, 29.4 mmol, 98%). IR (NaCI): 3412 (br), 3024 (w), 2981 (m), 2930 (w), 2873 (w), 1712 (m), 1613 (s), 1595 (m), 1519 (s), 1449 (m), 1377 (s), 1298 (m), 1266 (s), 1225 (s), 1149 (m), 1108 (s), 904 (m), 837 (m), 820 (m), 609 (m). $^1$H NMR (400 MHz, CDCl$_3$): δ 7.04 (d, J=8.4 Hz, 2H, aromatic CH), 6.74 (d, J=8.4 Hz, 2H, aromatic CH), 5.80 (s, 1H, ArOH), 5.00 (septet, J=6.3 Hz, 1H, (CH$_3$)$_2$CHO), 2.87 (t, J=7.6 Hz, 2H, CH$_2$CO$_2$iPr), 2.57 (t, J=7.6 Hz, 2H, ArCH$_2$), 1.20 (d, J=6.3 Hz, 6H, (CH$_3$)$_2$CHO). $^{13}$C NMR (100 MHz, CDCl$_3$): δ 172.97, 154.04, 132.19, 129.28, 115.19, 68.07 (d, Joc=9.8 Hz), 36.64, 30.23, 21.85. HRMS Calcd for C$_{12}$H$_{16}$O$_3$: 208.1099. Found: 208.1099. Anal. Calcd for C$_{12}$H$_{16}$O$_3$: C, 69.21; H, 7.74. Found: C, 69.43; H, 7.88.

Example 7

Synthesis of Isopropyl-1-(p-isopropoxyphenyl)propionate (25)

A solution of isopropyl-I-(p hydroxyphenyl)propionate (0.822 g, 3.95 mmol) in THF (10 mL) was treated via cannula with a suspension of sodium hydride (104 mg, 5.92 mmol, 1.1 equiv) in THF (10 mL) at 0° C. After gas evolution had subsided, DMF (20 mL) and 2-iodopropane (0.40 mL, 4.0 mmol, 1.0 equiv) were syringed into the reaction mixture. The resulting suspension was stirred at 22° C. for 6 hours, at which time additional sodium hydride (71.0 mg, 2.96 mmol. 0.75 equiv) in THF (5 mL) and 2-iodopropane (0.30 mL, 3.0 mmol, 0.75 equiv) were added. This procedure was repeated if necessary until no starting material could be detected by TLC analysis (we suspect that competing elimination of the electrophile is responsible for incomplete product conversions, requiring us to resubject the reaction mixture). The mixture was then diluted with Et$_2$O (150 mL) and water (200 mL) and transferred to a separatory funnel. The organic layer was removed, and the aqueous layer was washed twice with Et$_2$O (100 mL). The combined organic layers were washed with three volumes of water to remove residual DMF. The organic solution was then dried over MgSO$_4$, filtered, and concentrated in vacuo to a pale yellow oil. The product was passed through a short column of silica gel in 7:1 hexanes: Et$_2$O affording 811 mg (3.24 mmol, 82%) of a colorless oil (TLC Rf=0.30 in 7:1 hexanes:Et$_2$O). IR (NaCl): 2978 (m), 2934 (w), 1731 (s), 1612 (w), 1510 (s), 1452 (w), 1383 (m), 1295 (w), 1242 (s), 1182 (m), 1109 (s), 957 (w), 829 (w). $^1$H NMR (400 MHz, CDCl$_3$): δ 7.09 (d, J=8.6 Hz, 2H, aromatic CH), 6.80 (d, J=8.6 Hz, 2H, aromatic CH), 5.00 (septet, J=6.3 Hz, 1H, (CH$_3$)$_2$CHO$_2$C), 4.50 (septet, J=6.3 Hz, 1H, (CH$_3$)$_2$CHOAr), 2.87 (t, J=7.8 Hz, 2H, CH$_2$CO$_2$iPr), 2.55 (t, J=7.8 Hz, 2H, ArCH$_2$), 1.32 (d, J=6.3 Hz, 6H, (CH$_3$)$_2$CHOAr), 1.20 (d, J=6.3 Hz, 6H, (CH$_3$)$_2$CHO$_2$C). $^{13}$C NMR (100 MHz, CDCl$_3$): δ 172.39, 156.12, 132.43, 129.15, 115.81, 69.86 (d, J$_{OC}$=3.4 Hz), 67.59 (d, J$_{OC}$=9.8 Hz), 36.59, 30.26, 22.14, 21.88. HRMS Calcd for C$_{15}$H$_{22}$O$_3$: 250.1569. Found: 250.1566. Anal. Calcd for C$_{15}$H$_{22}$O$_3$: C, 71.97; H, 8.86. Found: C, 72.26; H, 9.04.

Example 8

Synthesis of
Isopropyl-1-(m-bromo-p-isopropoxyphenyl)propionate

A 50 mL round-bottom flask was charged with isopropyl-1-(p-isopropoxyphenyl)propionate (25) (1.09 g, 4.34 mmol) and CH$_2$Cl$_2$ (20 mL, 0.20 M). 10 mL of acetic acid (0.18 mmol) was added to the solution. Bromine (0.235 mL, 4.56 mmol, 1.05 equiv) was then slowly added dropwise via syringe, forming a red-colored solution. Over the course of 0.5 h, the solution gradually turned a pale yellow color as the bromine was consumed. After 1 h the reaction was quenched with 5 mL of saturated sodium thiosulfate. The mixture was diluted with water (200 mL) and Et$_2$O (200 mL) and partitioned in a separatory funnel. The aqueous layer was washed with 2×150 mL of Et$_2$O. The combined organic layers were dried over MgSO$_4$, filtered, and concentrated to a yellow oil. This material could be purified by vacuum distillation or silica gel chromatography (TLC R$_f$=0.23 in 10:1 hexanes: Et$_2$O) to deliver the product as a colorless oil (1.40 g, 4.25 mmol, 98%). Crucial to the success of this reaction is this use of exactly 1.0-1.1 equiv of bromine; an excess of the reagent leads to dibrominated adducts. If these impurities are generated, a CH$_2$Cl$_2$/pentane solvent system must be used as eluant to effect purification of the desired product on silica gel (TLC R$_f$=0.30 in 3:2 CH$_2$Cl$_2$:pentane). The halogenated solvent mix also promotes a facile separation of the product and the starting material (25) in the event that the reaction does not proceed to completion (<1.0 equiv Br$_2$). IR (NaCl) 2979 (m), 2936 (w), 1729 (s), 1604 (w), 1493 (s), 1384 (m), 1373 (m), 1281 (m), 1253 (s), 1240 (m), 1180 (m), 1140 (m), 1109 (s), 1046 (w), 954 (m), 812 (w). $^1$H NMR (400 MHz, CDCl$_3$): δ 7.38 (d, J=2.2 Hz, 1H, aromatic CH), 7.06 (dd, J=8.4, 2.2 Hz, 1H, aromatic CH), 6.83 (d, J=8.4 Hz, 1H, aromatic CH), 4.96 (septet, J=6.2 Hz, 1H, (CH$_3$)$_2$CHO$_2$C), 4.50 (septet, J=6.2 Hz, 1H, (CH$_3$)$_2$CHOAr), 2.85 (dd, J=7.7, 7.3 Hz, 2H, CH$_2$CO$_2$iPr), 2.55 (dd, J=7.7, 7.3 Hz, 2H, ArCH$_2$), 1.36 (d, J=5.9 Hz, 6H, (CH$_3$)$_2$CHOAr), 1.20 (d, J=6.6 Hz, 6H, (CH$_3$)$_2$CHO$_2$C). $^{13}$C NMR (100 MHz, CDCl$_3$): δ 172.06, 152.84, 134.36, 133.09 (d, J$_{OC}$=7.3 Hz), 128.03, 115.98, 113.63, 72.34 (d, J$_{OC}$=3.9 Hz), 67.80 (d, J$_{oc}$=12.2 Hz), 36.29, 29.90, 22.15 (d, J$_{oc}$ 2.4 Hz), 21.89 (d, J$_{oc}$ 3.4 Hz). HRMS Calcd for C$_{15}$H$_{21}$BrO$_3$: 328.0674. Found: 328.0671. Anal. Calcd for C$_{15}$H$_{21}$BrO$_3$: C, 54.72; H, 6.43. Found: C, 54.84; H, 6.43.

Example 9

Synthesis of
Isopropyl-1-(p-isopropoxy-m-vinylphenyl)propionate

Pd(PPh$_3$)$_4$ (166 mg, 0.144 mmol, 3 mol %) and 2,6-di-tert-butyl-4-methylphenol (1 mg, 0.005 mmol) were weighed into a 50 mL pear-shaped flask in a glove box and dissolved in 25 mL of dry toluene. This solution was transferred through a cannula into a neat sample of isopropyl-1-(m-bromo-p-pisopropoxyphenyl)propionate (1.58 g, 4.79 mmol) in a 50 mL round-bottom flask. The resulting pale yellow solution was stirred for 15 mm at 22 EC. Tributyl(vinyl)tin (1.54 mL, 5.27 mmol, 1.1 equiv) was then added dropwise to the reaction mixture through a syringe. The flask was equipped with a condenser and heated at 110° C. for 12 h. As the reaction progressed, a shiny mirror-like film of Bu$_3$SnBr salts was gradually deposited on the walls of the flask. After cooling to 22° C., the reaction mixture was passed through a small plug of celite and activated carbon using Et$_2$O as the eluant and concentrated in vacuo to give a yellow oil. Purification by silica gel chromatography (TLC R$_f$=0.27 in 8:1 hexanes: Et$_2$O) afforded 888 mg of a colorless oil (3.22 mmol, 67%). IR (NaCl): 2978 (s), 2936 (m), 2873 (w), 1731 (s), 1627 (w), 1491 (s), 1373 (m), 1246 (s), 1180 (m), 1109 (s), 996 (w), 957 (m), 904 (w), 814 (w). $^1$H NMR (400 MHz, CDCl$_3$): δ 7.31 (d, J=2.3 Hz, 1H, aromatic CH), 7.07-6.99 (m, 2H, aromatic CH and ArCHCH$_2$), 6.80 (d, J8.2 Hz, 1H, aromatic CH), 5.71 (dd, J=17.8, 1.6 Hz, 1H, ArCHCH$_2$), 5.22 (dd, J=11.3, 1.6 Hz, LH, ArCHCH$_2$), 5.00 (septet, J=6.3 Hz, 1H, (CH$_3$)$_2$CHO$_2$C), 4.49 (septet, J=6.3 Hz, 1H, (CH$_3$)$_2$CHOAr), 2.88 (dd, J=7.8, 7.4 Hz, 2H, CH$_2$CO$_2$iPr), 2.57 (dd, J=8.2, 7.4 Hz, 2H, ArCH$_2$), 1.33 (d, J=6.3 Hz, 6H, (CH$_3$)$_2$CHOAr), 1.21 (d, J=6.3 Hz, 6H, (CH$_3$)$_2$CHO$_2$C). $^{13}$C NMR (100 MHz, CDCl$_3$): δ 172.37, 153.50, 132.52, 131.81, 128.38, 127.67, 126.21 (d, J$_{OC}$ 5.4 Hz), 114.42, 113.76 (d, J$_{OC}$=8.3 Hz), 70.01 (d J$_{OC,}$ 3.4 Hz), 67.64 (d, J$_{OC}$ 11.2 Hz), 36.58, 30.40, 22.28, 21.93. HRMS Calcd for C$_{17}$H$_{24}$O$_3$: 276.1725. Found: 276.1716. Anal. Calcd for C$_{17}$H$_{24}$O$_3$: C, 73.88; H, 8.75. Found: C, 73.71; H, 8.73.

Example 10

Synthesis of
I-(p-isopropoxy-m-vinylphenyl)propionic Acid (26)

A 100 mL round-bottom flask was charged with isopropyl-1-(p-isopropoxy-m-vinylphenyl)propionate (462 mg, 1.67 mmol) and 66.8 mL of 1 M KOH (66.8 mmol, 40 equiv). The reaction vessel was equipped with a condenser and heated at 100° C. for 12 h. The mixture was then diluted with 100 mL of water, transferred to a 500 mL Erlenmeyer flask, and cooled to 0° C. The mixture was neutralized by the dropwise addition of ice-cold 1 M HCl. At a pH of ~7, 150 mL of Et$_2$O was added. The aqueous layer was acidified further to pH 3-4 with vigorous stirring, resulting in spontaneous precipitation of the product that immediately enters the organic phase. The layers were partitioned in a separatory funnel (an emulsion may form, requiring extended time for phase separation), and the aqueous layer was washed with additional Et$_2$O (150 mL). The pH of the aqueous layer was then lowered to ~2 in the presence of Et$_2$O. Again, the organic layer was collected and the aqueous layer was washed. The organic layers were pooled and washed with 500 mL of a saturated solution of sodium chloride. Drying over MgSO$_4$ and concentration in vacuo afforded 355 mg (1.52 mmol, 91%) of a light yellow solid which proved to be >98% pure as judged by $^1$H NMR spectroscopy (400 MHz). If necessary, the acid could be further purified by silica gel chromatography (TLC R$_f$=0.31 in 3:2 hexanes:Et$_2$O). It is recommended that the above procedure be followed with care since the product is quite prone to acid-catalyzed polymerization of the styrene moiety. Rapid, uncontrolled addition of the acid or acidification in the absence of Et$_2$O can result in complete loss of the product to polymerization. IR (NaCl): 2979 (m), 2935 (w), 2860 (w), 2760 (w), 1686 (s), 1600 (s), 1243 (s). $^1$H NMR (500 MHz, CDCl$_3$): δ 11.26 (br, 1H, CO$_2$H), 7.32 (d, J=2.3 Hz, 1H, aromatic CH), 7.06-7.00 (m, 2H, aromatic CH and ArCHCH$_2$), 6.81 (d, J=8.5 Hz, 1H, aromatic CH), 5.72 (dd, J=17.8, 1.5 Hz, 1H, ArCHCH$_2$), 5.23 (dd, J=11.0, 1.5 Hz, 1H, ArCHCH$_2$), 4.50 (septet, J=6.1 Hz, 1H, (CH$_3$)$_2$CHOAr), 2.90 (dd, J=8.0, 7.6 Hz, 2H, CH$_2$CO$_2$iPr), 2.67 (dd, J=8.0, 7.6 Hz, 2H, ArCH$_2$), 1.34 (d, J=6.2 Hz, 6H, (CH$_3$)$_2$CHOAr). $^{13}$C NMR (125 MHz, CDCl$_3$): δ 178.78, 153.77, 132.13, 131.88, 128.40, 127.87, 126.29, 114.48, 113.99, 70.99, 35.80, 29.88, 22.19. HRMS Calcd for C$_{14}$H$_{18}$O$_3$: 234.1256. Found: 234.1257. Anal. Calcd for C$_{14}$H$_{18}$O$_3$: C, 71.77; H, 7.74. Found: C, 71.71; H, 7.68.

Example 11

Synthesis of Tetraallylsilane (27)

A 250 mL 2-neck flask equipped with a condenser and addition funnel was charged with freshly prepared allylmagnesium bromide in Et$_2$O (92.3 mL of a 0.95 M solution, 87.7 mmol, 4.1 equiv). SiCl$_4$ (2.45 mL, 21.4 mmol) was slowly added to the solution of Grignard reagent through the addition funnel in 20 mL of Et$_2$O at 22° C. over the course of 1 h. After 12 h of reflux at 35° C., the reaction was cooled to 0° C. and quenched with 10 mL of a saturated solution of ammonium chloride. The mixture was diluted with water (200 mL) and Et$_2$O (100 mL) and transferred to a separatory funnel. The organic layer was collected and the aqueous layer was washed with 2×150 mL of Et$_2$O. The organic layers were dried over MgSO$_4$, filtered, and concentrated in vacuo into a colorless oil. This material was passed through a small plug of silica in hexanes (TLC R$_f$=0.9 in hexanes) and concentrated. Vacuum distillation afforded 3.33 g (17.3 mmol, 81%) of the product as a colorless oil. IR (NaCl): 3078 (m), 3060 (w), 2996 (w), 2972 (m), 2916 (w), 2882 (w), 1630 (s), 1419 (m), 1393 (m), 1195 (m), 1154 (m), 1037 (m), 991 (s), 930 (m), 893 (s), 810 (m), 601 (m). $^1$H NMR (400 MHz, CDCl$_3$): δ 5.80 (ddt, J=16.8, 10.2, 8.2 Hz, 4H, CH=CH$_2$), 4.94-4.87 (m, 8H, CH=CH$_2$), 1.61 (ddd, J=8.2, 1.4, 1.0 Hz, 8H, SiCH$_2$). $^{13}$C NMR (100 MHz, CDCl$_3$): δ 134.07, 113.93, 19.03. Anal. Calcd for C$_{12}$H$_{20}$Si: C, 74.92; H, 10.48. Found: C, 75.01; H, 10.32.

Example 12

Synthesis of Si[(CH$_2$)$_3$Si(Me)$_2$CH=CH$_2$]$_4$ (28)

A 0.1 M solution of H$_2$PtCl$_6$·6H$_2$O (Speier's catalyst)[34] was freshly prepared in anhydrous 2-propanol. The hydrosilylation could also be effected with Karstedt's catalyst.[35] A 25 mL round-bottom flask was charged with the tetraene (27)(762 mg, 3.96 mmol), HMe$_2$SiCl (2.00 mL, 18.0 mmol, 4.6 equiv), and THF (0.5 M, 8.0 mL). The platinum catalyst (10.0 mL, 0.010 mmol, 0.0025 equiv) was added dropwise by syringe and the colorless solution was heated at reflux (65° C.) for 12 h. After 20 mm of reaction, the mixture had turned dark green in color. Reaction progress was monitored readily by thin-layer chromatography; the starting material (TLC R$_f$=0.9 in hexanes) stains bright yellow with KMnO$_4$. Following the removal of solvent and excess silane in vacuo,$^1$H NMR analysis (400 MHz) of the unpurified mixture indicated that <5% of the α-substituted product was present and that the material was sufficiently pure for the subsequent alkylation step. Thus, the product was dissolved in 20 mL of Et$_2$O and transferred by cannula into a solution of freshly prepared allylmagnesium bromide (0.936 M, 17.8 mL, 16.7 mmol, 4.2 equiv). The reaction was stirred for 12 h at 22° C. and quenched with 10 mL of a saturated solution of ammonium chloride. The mixture was diluted with water (200 mL) and Et$_2$O (150 mL) and partitioned in a separatory funnel. The aqueous layer was washed with 2×100 mL of Et$_2$O. The combined organic layers were washed with a volume of saturated sodium chloride, dried over MgSO$_4$, and vacuum filtered through a coarse frit funnel containing celite. Removal of volatiles gave a crude light orange oil which was purified by silica gel chromatography (TLC R$_f$0.63 in hexanes). The product was recovered as a colorless oil (2.11 g, 3.56 mmol, 90%). IR (NaCl): 3077 (w), 2954 (m), 2913 (s), 2876 (m), 1630 (m), 1418 (w), 1250 (s), 1153 (m), 1034 (w), 990 (w), 932 (w), 893 (s), 844 (s), 698 (w), 629 (w). $^1$H NMR (400 MHz, CDCl$_3$): δ 5.78 (ddt, J=16.8, 10.2, 8.2 Hz, 4H, CH=CH$_2$), 4.87-4.79 (m, 8H, CH=CH$_2$), 1.51 (d, J=8.2 Hz, 8H, SiCH$_2$CH=CH$_2$), 1.32 (m, 8H, SiCH$_2$CH$_2$CH$_2$Si), 0.62-0.53 (m, 16H, SiCH$_2$CH$_2$CH$_2$Si), −0.02 (s, 24H, Si(CH$_3$)$_2$). $^{13}$C NMR (100 MHz, CDCl$_3$): δ 135.21, 112.47, 23.49, 19.93, 18.55, 17.54, −3.52. HRMS Calcd for C$_{32}$H$_{67}$Si$_5$: 591.4089 (M−H)+. Found: 591.4072. Anal. Calcd for C$_{32}$H$_{68}$Si$_5$: C, 64.78; H, 11.55. Found: C, 64.98; H, 11.55.

Example 13

Synthesis of Ar(CH$_2$)$_2$CO$_2$(CH$_2$)$_3$Si(Me)$_2$(CH$_2$)$_3$SiI$_4$ (29)

Si[(CH$_2$)$_3$Si(Me)$_2$CH=CH$_2$]$_4$ (28)(587 mg, 0.989 mmol) was weighed into a 50 mL round-bottom flask and dissolved in 10 mL of THF. This solution was treated by cannula with freshly prepared 9-BBN (527 mg, 4.69 mmol, 4.74 equiv) in 10 mL of THF. After 12 h of stirring at 22° C., 10 mL each of H$_2$O$_2$ (30% wt. solution in water), 2 M NaOH, and ethanol were added. The mixture was then allowed to stir an additional 12 h at 22° C. Water (100 mL) and Et$_2$O (100 mL) were added and the organic layer was removed. The aqueous layer was washed with 2×100 mL of Et$_2$O. The combined organic layers were dried over MgSO$_4$ and filtered. Removal of volatiles gave a crude oil that was purified by silica gel chromatography (TLC R$_f$=0.36 in EtOAc). $^1$H NMR analysis (400 MHz) indicated that the product contained minor impurities (including cyclooctadiol) which made characterization of the material difficult. Thus, the crude product was carried directly into the next step. The tetraol was transferred to a 25 mL round-bottom flask, dissolved in 15 mL of CH$_2$Cl$_2$, and cooled to 0° C. 1-(p-isopropoxy-m-vinylphenyl)propionic acid (26)(1.02 g, 4.35 mmol, 4.4 equiv), EDC (912 mg, 4.76 mmol, 4.8 equiv), and DMAP (61 mg, 0.50 mmol, 0.50 equiv) were then directly added in succession to the mixture as solids. The resulting mixture was stirred for 4 h and quenched with 2 mL of a 10% citric acid solution. Additional water was added (200 mL) and the aqueous layer was washed with 3×100 mL of Et$_2$O. The combined organic layers were washed with 1 volume each of a saturated solution of sodium chloride and water. Drying over MgSO$_4$, filtration, and concentration gave a crude oil which was purified by silica gel chromatography (TLC R$_f$0.36 in 4:1 hexanes:EtOAc). The desired tetra(ester) was recovered as a colorless oil (954 mg, 0.623 mmol, 63%). IR (NaCl): 2974 (m), 2951 (m), 2919 (s), 2873 (m), 2855 (m), 1735 (s), 1627 (w), 1491 (m), 1451 (w), 1384 (w), 1372 (w), 1293 (w), 1247 (s), 1139 (m), 1119 (m), 958 (w), 906 (w), 837 (m). $^1$H NMR (400 MHz, CDCl$_3$): 87.30 (d, J=2.4 Hz, 4H, aromatic CH), 7.02 (d, J=6.4 Hz, 4H, aromatic CH), 7.02 (dd, J=19.8, 9.4 Hz, 4H, ArCHCH$_2$), 6.79 (d, J=8.8 Hz, 4H, aromatic CH), 5.71 (dd, J=17.8, 1.6 Hz, 4H, ArCHCH$_2$), 5.21 (dd, J=11.4, 1.6 Hz, 4H, ArCHCH$_2$), 4.48 (septet, J=6.2 Hz, 4H, (CH$_3$)$_2$CHOAr), 4.01 (t, J=7.0 Hz, 8H, CO$_2$CH$_2$), 2.88 (t, J=7.8 Hz, 8H, ArCH$_2$CH$_2$CO$_2$), 2.59 (t, J=7.8 Hz, 8H, ArCH$_2$CH$_2$CO$_2$), 1.58 (m, 8H, CO$_2$CH$_2$CH$_2$CH$_2$Si(Me)$_2$), 1.36-1.25 (m, 8H, SiCH$_2$CH$_2$CH$_2$Si(Me)$_2$), 1.33 (d, J=5.6 Hz, 24H, (CH$_3$)$_2$CHOAr), 0.58-0.52 (m, 16H, CH$_2$Si(Me)$_2$CH$_2$), 0.47-0.42 (m, 8H, Si(CH$_2$)$_4$), −0.04 (s, 24H, Si(Me)$_2$). $^{13}$C NMR (100

MHz, $CDCl_3$): δ 172.77, 153.44, 132.40, 131.76, 128.30, 127.61, 126.14, 114.30, 113.78, 70.96, 67.16, 36.30, 30.38, 23.33, 22.33, 20.20, 18.65, 17.63, 11.30, −3.26. LRMS Calcd for $C_{88}H_{140}O_{12}Si_5K$ (M+K): 1569.9. Found: 1569.5. Anal. Calcd for $C_{88}H_{140}O_{12}Si_5$: C, 69.06; H, 9.22. Found: C, 69.31; H, 9.36.

Example 14

Synthesis of [(PCy$_3$)Cl$_2$Ru=CH-o-O-i-PrC$_6$H$_3$(CH$_2$)$_2$COO(CH$_2$)$_3$Si(Me)$_2$CH$_{23}$Si]$_4$ (Formula 30)

(PCy$_3$)$_2$Cl$_2$Ru=CHPh (2)(792 mg, 0.962 mmol, 4.3 equiv) and CuCl (106 mg, 1.07 mmol, 4.8 equiv) were added to a 25 mL round-bottom flask and suspended in 12 mL of $CH_2Cl_2$. Dendrimer 29 (341 mg, 0.223 mmol, 1.0 equiv) was added to this mixture through a cannula in 10 mL of $CH_2Cl_2$. The mixture was stirred for a period of 3 h at 22° C., during which time the original purple solution turned dark brown in color. The following work-up procedures were conducted in air with reagent-grade solvents. The mixture was concentrated at reduced pressure and passed through a short plug of silica gel in 3:2 hexanes:$Et_2O$ (brown band rapidly elutes). Product fractions were pooled and concentrated. This material was passed through a second column of silica gel, this time with a gradient elution (1:1 hexanes:$CH_2Cl_2$ to 2:3 hexanes:$CH_2Cl_2$ to 1:3 hexanes:$CH_2Cl_2$ to 100% $CH_2Cl_2$). Finally, the column was flushed with $Et_2O$, at which point the product elutes (brown band). Solvent removal afforded a dark brown crystalline solid (637 mg, 0.194 mmol, 87%). IR (NaCl): 2927 (s), 2852 (s), 1955 (w), 1733 (s), 1684 (w), 1610 (w), 1582 (w), 1488 (m), 1447 (m), 1417 (w), 1385 (m), 1296 (w), 1247 (m), 1222 (m), 1204 (m), 1134 (m), 1104 (m), 913 (w), 891 (w), 849 (m), 774 (w), 735 (m), 702 (w). $^1$H NMR (400 MHz, $CDCl_3$): δ 17.38 (d, J=4.0 Hz, 4H, Ru=CHAr), 7.52 (s, 4H, aromatic CH), 7.46 (d, J=8.8 Hz, 4H, aromatic CH), 6.98 (d, J=8.8 Hz, 4H, aromatic CH), 5.23 (septet, J=6.2 Hz, 4H, (CH$_3$)$_2$CHOAr), 4.03 (t, J=7.1 Hz, 8H, CO$_2$CH$_2$), 3.03 (t, J=7.7 Hz, 8H, ArCH$_2$CH$_2$CO$_2$), 2.64 (t, J=7.7 Hz, 8H, ArCH$_2$CH$_2$CO$_2$) 2.32 (m, 12H, PCH), 2.20-1.20 (m, 136H, CO$_2$CH$_2$CH$_2$CH$_2$Si(Me)$_2$, SiCH$_2$CH$_2$CH$_2$Si(Me)$_2$, and P(CH(CH$_2$)$_5$)$_3$), 1 79 (d, J=6.2 Hz, 24H, (CH$_3$)$_2$CHOAr), 0.60-0.52 (m, 16H, CH$_2$Si(Me)$_2$CH$_2$), 0.50-0.45 (m, 8H, Si(CH$_2$)$_4$), −0.03 (s, 24H, Si(Me)$_2$). $^{13}$C NMR (100 MHz, $CDCl_3$): δ 279.24, 172.60, 151.29, 143.79, 134.69, 129.42, 122.51 (d, J$_{OC}$=5.9 Hz), 113.19, 75.50 (d, J$_{OC}$=7.8 Hz), 67.27, 36.36, 35.67 (d, J$_{PH}$=24.4 Hz), 30.14, 29.73, 27.80 (d, J$_{PH}$=10.7 Hz), 26.33, 23.26, 22.14, 20.14, 18.58, 17.56, 11.26, −3.33. $^{31}$P NMR (162 MHz, $CDCl_3$): δ59.17 (s, PCy$_3$). LRMS Calcd for $C_{156}H_{264}Cl_8O_{12}P_4Ru_4Si_5Na_2$ (M+2Na)+: 3331.2. Found: 3331.8. Anal. Calcd for $C_{156}H_{264}Cl_8O_{12}P_4Ru_4Si_5$: C, 57.05; H, 8.10. Found: C, 56.80; H, 8.00.

Example 15

Synthesis of [(4,5-dihydroIMES) Cl$_2$ Ru=CH-o-O-i-PrC$_6$H$_3$(CH$_2$)$_2$COO(CH$_2$)$_3$Si(Me)$_2$(CH$_2$)$_3$Si]$_4$ (formula 31)

The unmetallated dendrimer (29) (227 mg, 0.148 mmol, 1.0 equiv) was weighed into a 25 mL round-bottom flask and dissolved in 15 mL of $CH_2Cl_2$. (4,5-dihydroIMES)(PCy$_3$)Cl$_2$Ru=CHPh (3)(606 mg, 0.714 mmol, 4.8 equiv) and CuCl (72.0 mg, 0.731 mmol, 4.9 equiv) were added directly to this solution as solids. The mixture was stirred for 2 h at 22° C., during which time the original purple solution turned a dark green/brown color. The following work-up procedures were conducted in air using reagent grade solvents. The mixture was concentrated at reduced pressure and passed through a short column of silica gel using a gradient elution (100% $CH_2Cl_2$ to 4:1 hexanes:$Et_2O$ to 1:1 hexanes: $Et_2O$ to 100% $Et_2O$). The green band was collected and concentrated, affording a green microcrystalline solid (277 mg, 0.08 16 mmol, 55%). IR (NaCl): 3432 (b), 2915 (m), 1732 (s), 1632 (w), 1607 (w), 1595 (w), 1487 (s), 1418 (m), 1259 (s), 1221 (m), 1132 (m), 1104 (m), 1034 (w), 912 (w), 849 (w), 579 (w). $^1$H NMR (300 MHz, $CDCl_3$): δ 16.51 (s, 4H, Ru=CHAr), 7.33 (d, J=7.0 Hz, 4H, aromatic CH), 7.07 (s, 16H, mesityl aromatic CH), 6.74-6.66 (m, 8H, aromatic CH), 4.85 (septet, J=6.3 Hz, 4H, (CH$_3$)$_2$CHOAr), 4.17 (s, 16H, N(CH$_2$)$_2$N), 4.02 (t, J=7.0 Hz, 8H, CO$_2$CH$_2$), 2.91 (t, J=7.8 Hz, 8H, ArCH$_2$CH$_2$CO$_2$), 2.53 (t, J=7.8 Hz, 8H, ArCH$_2$CH$_2$CO$_2$), 2.47 (s, 48H, mesityl o-CH$_3$), 2.41 (s, 24H, mesityl pCH$_3$), 1.61 (m, 8H, CO$_2$CH$_2$CH$_2$CH$_2$Si(Me)$_2$), 1.40-1.25 (m, 8H, SiCH$_2$CH$_2$CH$_2$Si(Me)$_2$), 1.24 (d, J=6.3 Hz, 24H, (CH$_3$)$_2$CHOAr), 0.61-0.45 (m, 24H, CH$_2$Si(Me)$_2$CH$_2$ and Si(CH$_2$)$_4$), −0.02 (s, 24H, Si(Me)$_2$). $^{13}$C NMR (75 MHz, $CDCl_3$): δ 297.07 (d, J=166.0 Hz), 211.32, 172.81, 150.80, 145.16, 138.76, 134.28, 130.42, 130.29, 129.80, 129.39, 128.74, 128.22, 74.41, 67.19, 51.44, 36.03, 29.54, 23.14, 21.53, 20.96, 20.60, 20.03, 18.48, 17.47, 11.12, −4.13. LRMS Calcd for $C_{168}H_{240}Cl_8N_8O_{12}Ru_4Si_5$ (M+4H): 3393.1. Found: 3393.1. Anal. Calcd for $C_{168}H_{236}Cl_8N_8O_{12}Ru_4Si_5$: C, 59.56; H, 7.02. Found: C, 59.55; H, 6.96.

Example 16

Representative Experimental Procedure for RCM Catalyzed by Monomer (4,5 dihydroIMES) Cl$_2$Ru=CH-o-O-i-PrC$_6$H$_4$ (formula 5)

Triene (7)(50.1 mg, 0.329 mmol, 1.0 equiv) was weighed out in a 25 mL round-bottom flask and dissolved in 3 mL of $CH_2Cl_2$ (0.1 M). (4,5-dihydroIMES)Cl$_2$RuCH-o-O-i-PrC$_6$H$_4$ (5)(9.80 mg, 0.0 156 mmol, 0.0474 equiv) was added as a solid and the resulting deep green solution was stirred at 22° C. TLC analysis after 10 mm indicated completion of the reaction. As usual, work-up procedures were conducted in air using reagent-grade solvents. The mixture was concentrated at reduced pressure and passed through a short column of silica gel in 2:1 hexanes:$CH_2Cl_2$ affording diene (8)(33.4 mg, 0.269 mmol, 82%) as a colorless oil (TLC R$_f$=0.46 in 9:1 hexanes:$Et_2O$). The catalyst was then retrieved as a green solid by flushing the silica column with 100% $CH_2Cl_2$ (9.60 mg, 0.0 153 mmol, 98%).

Example 17

Representative Experimental Procedure for RCM Catalyzed by Dendritic [(PCY$_3$)Cl$_2$Ru=CH-o-O-i-PrC$_6$H$_3$(CH$_2$)$_2$COO(CH$_2$)$_3$Si(Me)$_2$(CH$_2$)$_3$Si]$_4$ (formula 30)

Tosyl amide (32)(250 mg, 0.995 mmol, 1.0 equiv) and dendritic catalyst (30)(43.9 mg, 0.0140 mmol, 0.0 14 equiv) were weighed into a 50 mL round-bottom flask. The flask was equipped with a reflux condenser, evacuated, and filled with an atmosphere of argon. The vessel was charged with $CH_2Cl_2$ (20 mL, 0.05 M) and submerged into an oil bath preheated to 45° C. The reaction was stirred for 15 minutes, at which point TLC analysis indicated completion of the reaction. Removal of the solvent in vacuo afforded a dark brown oil that was purified by silica gel chromatography (100% $CH_2Cl_2$), affording 33 as a white solid (219 mg, 0.983 mmol, 99%). The column was then flushed with 100% $Et_2O$ to recover the dendritic catalyst as a brown solid residue (46.2 mg, 0.0141 mmol, 100%). The recovered catalyst was transferred directly into a new flask for a subsequent reaction. As discussed above, Ru recovery on the dendrimer could be quickly analyzed upon inspection of the $^1$H NMR (400 MHz) spectrum. Integration of the benzylic methylene protons at 3.03 ppm (metal-occupied sites) and 2.88 ppm (metal-vacant sites) provided a ratio of 88:12 respectively.

Example 18

Experimental Procedure for RCM Catalyzed by Dendritic [(4,5-dihydroIMES)$Cl_2$Ru=CH-o-O-i-$PrC_6H_3$ $(CH_2)_2COO(CH_2)_3Si(Me)_2(CH_2)_3$ $Si]_4$ (formula 31)

Diene (11)(32.7 mg, 0.233 mmol, 1.0 equiv) was weighed into a 25 mL round-bottom flask and dissolved in 5 mL of $CH_2Cl_2$ (0.05 M). Dendritic catalyst 31 (12.4 mg, 0.00366 mmol, 0.016 equiv) was added as a solid and the solution was allowed to stir at 22° C. TLC analysis after 2 h indicated completion of the reaction. Work-up procedures proceeded in air with reagent-grade solvents. The mixture was concentrated at reduced pressure and passed through a short plug of silica gel in 100% $CH_2Cl_2$, affording (12)(20.4 mg, 0.1819 mmol, 78%) as a colorless oil (TLC $R_f$=0.25 in 4:1 hexanes: $Et_2O$). The catalyst was then flushed off of the column with 100% $Et_2O$ affording 12.3 mg (0.00363 mmol, 99%) of a green solid. Ru recovery on the dendrimer was assessed using $^1$H NMR spectroscopy (400 MHz). Integration of the isopropoxy methine proton for both metal-occupied (4.90 ppm) and metal-vacant (5.71 ppm) sites gave a ratio of 92:8 respectively, indicative of 8% metal loss.

Example 19

Synthesis of an Immobilized Catalyst

This procedure allows installment of the linker and the active metal complex in a single step. Treatment of the compound 35 with a stoichiometric amount of (4,5-dihydroIMES)($PCy_3$) $Cl_2$Ru=CHPh in the presence of allylchlorodimethylsilane led to successful ring-opening cross metathesis and metallation of the styrenyl ether "docking site." Subsequent diffusion of this product into the pores of a sol gel sample (200 A° pore size glass monoliths, available from Geltech, Orlando, Fla.) resulted in a substitution reaction involving the labile Si—Cl bond with the free hydroxyl groups on the glass surface. After extensive washing and drying in vacuo, a bright green glass pellet (Formula 6) was recovered which showed good activity in the RCM of the terminal diene 44 (0.10 mmol scale) to yield 45 (as shown in Scheme 7). The immobilized catalyst was then carried through three iterative rounds of metathesis to covert diene 44 to the cyclic compound 45 as shown below.

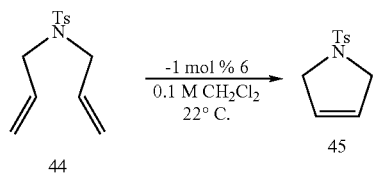

Although successive ring-closures required longer reaction times, >90% conversion was observed in each case, the following factors were observed: (1) Derivatization of the sol gel pellet resulted in a 1.0 mg increase in mass. Calculations therefore suggest that the RCM of compound 7 was mediated by a very small amount of active catalyst (~1 mol %). This may partly account for the slow reaction rate, particularly in the second and third cycles. Increasing the catalyst loading to 5 mol % will lead to dramatic improvements in reaction rate. (2) In contrast to reactions run with 5 mol % Formula 1 or 5, the spectrum of the unpurified reaction mixture consisted of >98% pure cycloolefin (no catalyst or byproduct thereof could be detected). (3) No filtration step was required to isolate the product. The reaction mixture was simply removed with a Pasteur pipette, the glass sample was washed with $CH_2Cl_2$, and fresh substrate was added.

Although the invention has been described in detail for the purpose of illustration, it is understood that such detail is solely for this purpose, and variations can be made therein by those skilled in the art without departing from the spirit and scope of the invention as described by the appended claims.

What is claimed is:

1. A transition metal catalyst comprising:
a substrate having at least one functional group;
a transition metal having at least one substituent that reacts with at least one functional group on the substrate to chemically bond the transition metal to the substrate,
wherein the transition metal catalyst has the following structure:

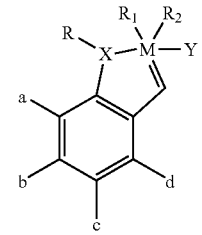

wherein:
M comprises a transition metal;
R comprises an alkyl, alkenyl, alkynyl, aryl, alkoxy, alkenyloxy, alkynyloxy, aryloxy, alkoxy carbonyl, alkylamino, alkylthio, alkylsulfonyl, alkylsulfinyl; each optionally substituted with an alkyl, halogen, alkoxy, aryl or heteroaryl moiety;
$R_1$ and $R_2$ each comprises or together comprise, an electron withdrawing anionic ligand;
a, b, c, and d each comprise H, a halogen atom or an alkyl, alkenyl, alkynyl, aryl, alkoxy, alkenyloxy, alkynyloxy, aryloxy, alkoxycarbonyl, alkylamino, alkylthio, alkylsulfonyl; alkylsulfinyl; each optionally substituted with an alkyl, halogen, aryl or heteroaryl moiety;
X is oxygen, sulfur, nitrogen or phosrhorus; and
Y comprises an electron-donating heterocyclic carbene ligand.

2. The transition metal catalyst of claim 1 wherein the substituent is selected from the group consisting of alkyl halosilanes, alkenyl halosilanes, alkoxy halosilanes, aryloxy halosilanes, aryl halosilanes, alkyl halides, cycloalkyl halides, alkenyl halides, cycloalkenyl halides, aromatic and heteroaromatic halides, acid chlorides, anhydrides, succimidyl esters, epoxides, thiols, acrylate, methacrylate, acrylamide, methacrylamide, benzophenone, and derivatives thereof.

3. The transition metal catalyst of claim 1 wherein the substituent is allyldimethylsilylchloride.

4. The transition metal catalyst of claim 1 wherein the substrate is a porous or a non-porous solid phase.

5. The transition metal catalyst of claim 1 wherein the substrate is selected from the group consisting of glasses, metals, non-metals, ceramics, rubbers and polymeric materials.

6. The transition metal catalyst of claim 1 wherein the substrate is part of a containing vessel.

7. A transition metal catalyst having the following structure:

$$R_7-\underset{\underset{R_6}{|}}{\overset{\overset{R_8}{|}}{A}}-R_5$$

wherein A is a polyvalent atom selected from the group consisting of carbon, nitrogen, silicon and phosphorous;
wherein $R_5$, $R_6$, $R_7$ and $R_8$ each comprises the following structure:

[structure shown]

wherein:
M comprises a transition metal;
X comprises oxygen, sulfur, nitrogen or phosphorus;
R comprises an alkyl, alkenyl, alkynyl, aryl, alkoxy, alkenyloxy, alkynyloxy, aryloxy, alkoxy carbonyl, alkylamino, alkylthio, alkylsulfonyl, or alkylsulfinyl; each optionally substituted with an alkyl, halogen, aryl or heteroaryl moiety;
$R_1$ and $R_2$ each comprises, or together comprise, an electron withdrawing group; and
Z comprises an electron-donating heterocyclic carbene ligand or a phosphine group.

8. The transition metal catalyst of claim 7 wherein A is silicon.

9. The transition metal catalyst of claim 7 wherein M is a transition metal selected from the group consisting of ruthenium, osmium and tungsten.

10. The transition metal catalyst of claim 7 wherein M is ruthenium.

11. The transition metal catalyst of claim 7 wherein X is oxygen.

12. The transition metal catalyst of claim 7 wherein R is a lower alkyl group.

13. The transition metal catalyst of claim 7 wherein R is isopropyl.

14. The transition metal catalyst of claim 7 wherein each of $R_1$ and $R_2$ is a halogen.

15. The transition metal catalyst of claim 7 wherein each of $R_1$ and $R_2$ is chlorine.

16. The transition metal catalyst of claim 7 wherein Z comprises a phosphine moiety having the formula $P(Cy)_3$.

17. The transition metal catalyst of claim 7 wherein Z comprises an aromatic ring structure having the following structure:

[structure shown]

wherein $R_3$ and $R_4$ each comprises an aromatic ring moiety.

18. The transition metal catalyst of claim 1, wherein the transition metal is selected from the group consisting of ruthenium, osmium and tungsten.

19. The transition metal catalyst of claim 2 wherein the substituent is selected from the group consisting of alkyl halosilanes, alkenyl halosilanes, alkoxy halosilanes, aryloxy halosilanes, aryl halosilanes, alkyl halides, cycloalkyl halides, alkenyl halides, cycloalkenyl halides, aromatic and heteroaromatic halides, acid chlorides, anhydrides, succimidyl esters, epoxides, acrylamide, methacrylamide, and benzophenone.

20. A transition metal catalyst having the following structure:

[structure shown]

wherein:
M comprises a transition metal;
R comprises an alkyl, alkenyl, alkynyl, aryl, alkoxy, alkenyloxy, alkynyloxy, aryloxy, alkoxy carbonyl, alkylamino, alkylthio, alkylsulfonyl, alkylsulfinyl; each optionally substituted with an alkyl, halogen, alkoxy, aryl or heteroaryl moiety;
$R_1$ and $R_2$ each comprises or together comprise, an electron withdrawing anionic ligand;
a, b, c, and d each comprise H, a halogen atom or an alkyl, alkenyl, alkynyl, aryl, alkoxy, alkenyloxy, alkynyloxy, aryloxy, alkoxycarbonyl, alkylamino, alkylthio, alkylsulfonyl; alkylsulfinyl; each optionally substituted with an alkyl, halogen, aryl or heteroaryl moiety;
X is oxygen, sulfur, nitrogen or phosphorus; and
Y comprises an electron-donating heterocyclic carbene ligand.

21. The transition metal catalyst of claim 20 wherein M is Ru.

22. The transition metal catalyst of claim 20 wherein X is O.

23. The transition metal catalyst of claim 20 wherein R is a lower alkyl group.

24. The transition metal catalyst of claim 23 wherein R is isopropyl.

25. The transition metal catalyst of claim 20 wherein $R_1$ and $R_2$ each is a halogen.

26. The transition metal catalyst of claim 25 wherein $R_1$ and $R_2$ each is Cl.

27. The transition metal catalyst of claim 20 wherein a, b, c, and d each comprises H or a lower alkyl group.

28. The transition metal catalyst of claim 20 wherein Y comprises a 4,5-dihydroimidazol-2-ylidene.

29. The transition metal catalyst of claim 28 wherein Y comprises a tricyclic aromatic ring structure having the following structure:

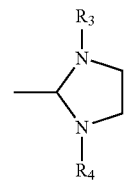

wherein $R_3$ and $R_4$ each comprises an aromatic ring moiety.

30. The transition metal catalyst of claim 29 wherein $R_3$ and $R_4$ both comprise 2,4,6-trimethylphenyl (mesityl) moieties.

* * * * *